(12) United States Patent
Niitsu et al.

(10) Patent No.: US 9,408,864 B2
(45) Date of Patent: Aug. 9, 2016

(54) COMPOSITION FOR REGENERATING NORMAL TISSUE FROM FIBROTIC TISSUE

(75) Inventors: Yoshiro Niitsu, Sapporo (JP); Akihiro Yoneda, Sapporo (JP); Hirotoshi Ishiwatari, Sapporo (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/813,907

(22) PCT Filed: Aug. 5, 2011

(86) PCT No.: PCT/JP2011/067953
§ 371 (c)(1),
(2), (4) Date: Mar. 19, 2013

(87) PCT Pub. No.: WO2012/018115
PCT Pub. Date: Feb. 9, 2012

(65) Prior Publication Data
US 2013/0172401 A1 Jul. 4, 2013

(30) Foreign Application Priority Data
Aug. 5, 2010 (JP) ................ 2010-175920
Oct. 12, 2010 (JP) ................ 2010-230020

(51) Int. Cl.
| | | |
|---|---|---|
| A61K 31/713 | (2006.01) | |
| A61K 9/00 | (2006.01) | |
| A61K 9/127 | (2006.01) | |
| A61K 31/41 | (2006.01) | |
| A61K 31/55 | (2006.01) | |
| A61K 45/06 | (2006.01) | |

(52) U.S. Cl.
CPC ............ *A61K 31/713* (2013.01); *A61K 9/0019* (2013.01); *A61K 9/1272* (2013.01); *A61K 31/41* (2013.01); *A61K 31/55* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,966,773 A | 10/1990 | Gressel et al. | |
| 5,643,584 A | 7/1997 | Farng et al. | |
| 5,811,119 A | 9/1998 | Mehta et al. | |
| 5,851,538 A | 12/1998 | Froix et al. | |
| 6,183,774 B1 | 2/2001 | Aust et al. | |
| 8,173,170 B2 | 5/2012 | Niitsu et al. | |
| 8,178,124 B2 | 5/2012 | Niitsu et al. | |
| 8,574,623 B2 | 11/2013 | Niitsu et al. | |
| 8,652,526 B2 | 2/2014 | Niitsu et al. | |
| 8,686,052 B2 | 4/2014 | Niitsu et al. | |
| 2002/0012998 A1 | 1/2002 | Gonda et al. | |
| 2003/0096739 A1 | 5/2003 | Morris | |
| 2003/0161791 A1 | 8/2003 | Bentley et al. | |
| 2003/0211143 A1 | 11/2003 | Liu et al. | |
| 2004/0028682 A1 | 2/2004 | Border et al. | |
| 2005/0004064 A1 | 1/2005 | Tei et al. | |
| 2005/0165227 A1 | 7/2005 | Vlahov et al. | |
| 2006/0013775 A1 | 1/2006 | Gristwood et al. | |
| 2006/0074041 A1 | 4/2006 | Johnston et al. | |
| 2008/0057030 A1 | 3/2008 | Crager | |
| 2008/0193512 A1 | 8/2008 | Niitsu et al. | |
| 2008/0279765 A1 | 11/2008 | Chettibi et al. | |
| 2009/0010918 A1* | 1/2009 | Badalemente et al. .... 424/94.67 |
| 2009/0105179 A1 | 4/2009 | Yu et al. | |
| 2009/0232781 A1 | 9/2009 | Fu | |
| 2010/0028416 A1 | 2/2010 | Yu et al. | |
| 2011/0104255 A1 | 5/2011 | Niitsu et al. | |
| 2011/0178157 A1 | 7/2011 | Jin et al. | |
| 2011/0229558 A1 | 9/2011 | Niitsu et al. | |
| 2012/0269886 A1 | 10/2012 | Niitsu et al. | |
| 2012/0328694 A1 | 12/2012 | Niitsu et al. | |
| 2013/0011336 A1 | 1/2013 | Niitsu et al. | |
| 2013/0045272 A1 | 2/2013 | Niitsu et al. | |
| 2013/0136789 A1 | 5/2013 | Niitsu et al. | |
| 2013/0171127 A1 | 7/2013 | Niitsu et al. | |
| 2013/0171240 A1 | 7/2013 | Niitsu et al. | |
| 2013/0172401 A1 | 7/2013 | Niitsu et al. | |
| 2013/0210744 A1 | 8/2013 | Niitsu et al. | |
| 2013/0216611 A1 | 8/2013 | Niitsu et al. | |
| 2013/0267581 A1 | 10/2013 | Niitsu et al. | |
| 2014/0127187 A1 | 5/2014 | Niitsu et al. | |
| 2014/0315975 A1 | 10/2014 | Niitsu et al. | |
| 2014/0323550 A1 | 10/2014 | Ayabe et al. | |

FOREIGN PATENT DOCUMENTS

| | | |
|---|---|---|
| CN | 101102795 A | 1/2008 |
| EP | 0784980 | 7/1997 |
| EP | 1842557 | 10/2007 |
| EP | 2583691 A1 | 4/2013 |
| EP | 2609922 A1 | 7/2013 |

(Continued)

OTHER PUBLICATIONS

Watanabe, et al., Treatment of idiopathic myelofiosis employing siRNA for heat shock protein 7 (siRNA/HSP47) encapsulated in liposomes, Blood (2007) 110:235.
Extended European Search Report dated Dec. 6, 2013 for EP Application No. 11814740.4, filed Aug. 5, 2011.
Ishiguro, T., et al., "Intercalation activating fluorescence DNA probe and its application to homogenous quantification of a target sequence by isothermal sequence amplification in a closed vessel" Anal. Biochem. (2003) 314: 77-86.
Examination Report dated Mar. 4, 2014, for Japanese Application No. 2010-230020, filed Aug. 5, 2011.

(Continued)

*Primary Examiner* — Tracy Vivlemore
(74) *Attorney, Agent, or Firm* — Knobbe Martens Olson & Bear LLP

(57) ABSTRACT

The present invention relates to a pharmaceutical composition and a method for regenerating normal tissue from fibrotic tissue, the pharmaceutical composition and the method employing a collagen-reducing substance. In accordance with the present invention, normal tissue can be therapeutically regenerated from fibrotic tissue.

8 Claims, 19 Drawing Sheets

(56) References Cited

FOREIGN PATENT DOCUMENTS

| | | |
|---|---|---|
| JP | 7-300426 | 7/1995 |
| JP | 08-268906 | 10/1996 |
| JP | 11-269076 | 10/1999 |
| JP | 2002-047211 | 2/2002 |
| JP | 2002-363094 | 12/2002 |
| JP | 2002-371006 | 12/2002 |
| JP | 2003-119138 | 4/2003 |
| JP | 2003-219893 | 8/2003 |
| WO | WO 91/04748 | 4/1991 |
| WO | WO 00/64478 | 11/2000 |
| WO | WO 03/009881 | 2/2003 |
| WO | WO 03/045383 | 6/2003 |
| WO | WO 2004/001381 | 12/2003 |
| WO | WO 2004/019921 | 3/2004 |
| WO | WO 2004/069159 | 8/2004 |
| WO | WO 2004/090108 | 10/2004 |
| WO | WO 2005/082402 | 9/2005 |
| WO | WO 2006/068232 | 6/2006 |

OTHER PUBLICATIONS

Examination Report dated Jan. 13, 2014 in Australian Patent Application No. 2011286636, filed on Aug. 5, 2011.
Anan et al. "Proteasome Inhibition Induces Hepatic Stellate Cell Apoptosis" Hepatology (2000) 43(2):335-344.
Benedetti, A. et al., "Inhibition of the Na+/H+ exchanger reduces rat hepatic stellate cell activity and liver fibrosis: an in vitro and in vivo study," Gastroenterology (2001)120(2):545-56.
Gallo et al., "Antidiabetic Thiazolidineiones Inhibit Collagen Synthesis and Hepatic Stellate Cell Activation in Vivo and in Vitro" Gastroenterology (2002):1924-1940.
George, J. et al., "In vivo inhibition of rat stellate cell activation by soluble transforming growth factor p type II receptor: A potential new therapy for hepatic fibrosis," Proc. Nat. Acad. Sci. USA (Oct. 1999) 96(22):12719-24.
Iimuro, Y. et al., "Delivery of matrix metalloproteinase-1 attenuates established liver fibrosis in the rat," Gastroenterology (2003) 124:445-458.
Iimuro et al., "Treatment for Existing Hepatic Fibrosis by Means of MMP-1 Gene Introduction" Bio Clinica (2001) 16(4):330-334.
Iredale, J. P., "Models of liver fibrosis: exploring the dynamic nature of inflammation and repair in a solid organ" J Clin Invest (2007) 117(3):539-548.
Issa et al., "Spontaneous Recovery From Micronodular Cirrhosis: Evidence for Incomplete Resolution Associated With Matrix Cross-Linking" Gastroenterology (2004) 126(7):1795-1808.
Parsons et al., "Antifibrotic Effects of a Tissue Inhibitor of Metalloproteinase-1 Antibody on Established Liver Fibrosis in Rats" Hepatology (2004) 40(5):1106-1115.
Sato, et al, "Resolution of liver cirrhosis using vitamin A-coupled liposomes to deliver siRNA against a collagen-specific chaperone," Nature Biotechnology (2008) 26(4):431-442.
Sato et al, "Possibility of Treating Fibrosis by Inhibiting Collagent Production" Kan Tan Sui (2008) 57(2):299-304.
Ueki, K. et al., "Hepatocyte growth factor gene therapy ofliver cirrhosis in rats," Nat. Med. (Feb. 1999) 5(2):226-30.
International Search Report and Written Opinion issued on Aug. 30, 2011 for PCT/JP2011/067953, filed Aug. 5, 2011.
Office Action dated May 5, 2014, for Chinese Application No. 201180038574.2, filed Aug. 5, 2011.
Office Action dated Jan. 23, 2015, for Chinese Application No. 201180038574.2, filed Aug. 5, 2011.
Office Action dated Oct. 7, 2014, for Japanese Application No. 2010-230020, filed Aug. 5, 2011.
Office Action dated Feb. 26, 2015, for Taiwanese Application No. 100127765, filed Aug. 4, 2011.
Kuang Yuyu, "Different concentrations of hepatocyte growth factor and fibroblast growth factor in the regulation of hepatic stem cells in rats" International Journal of Pathology and Clinical Medicine (2010) 30(2):106-109.

Andrew, E.R., et al., "Molecular motion in solid all-trans retinoic acid (vitamin A acid) by proton NMR." Solid State Nuclear Magnetic Resonance 13, pp. 39-43, 1998.
Apte et al. "Periacinar stellate shaped cells in rat pancreas: identification, isolation and culture." Gut 1998;43:128-133.
Belijaars, et al. "Albumin Modified with Mannose 6-Phosphate: A Potential Carrier for Selective Delivery of Antifibrotic Drugs to Rat and Human Hepatic Stellate Cells." Hepatology vol. 29, No. , pp. 1486-1493, 1999.
Blomhoff et al., "Hepatic Uptake of [H] Retinol Bound to the Serum Retinol Binding Protein Involves Both Parenchymal and Perisinusoidal Stellate Cells, " The Journal of Biological Chemistry 1985; 260(25): 13571-13575.
Blomhoff, Rune, et al., Newly Administered [$^3$H] Retinol is Transferred from Hepatocytes to Stellate Cells in Liver for Storage. Experimental Cell Research, vol. 150, pp. 186193, 1984.
Devi, GR. "siRNA-based Approaches in Cancer Therapy", Cancer Gene Therapy (2006) 13, 819-29.
Dixon et al., "Nomenclature of Retinoids." Pure & Appl. Chem., vol. 55, No. 4, pp. 721-726 (1983).
Dunham et al., Membrane fusion: Studies with a calcium-sensitive dye, arsenazo III, in liposomes. Proceedings of the National Academy of Science, USA, vol. 74, No. 4, pp. 1580-1584, 1997.
Fortuna V.A. et al., "Hepatic Stellate Cells Uptake of Retinol Associated With Retinol-Binding Protein or With Bovine Serum Albumin," Journal of Cellular Biochemistry 2003; 90(4):792-805.
Friedman, S. L., "Targeting siRNA to arrest fibrosis," Nature Biotechnology (Apr. 2008) 26(4): 399-400.
George et al. "In vivo inhibition of rat stellate cell activation by soluble transforming growth factor beta type II receptor: A potential new therapy for hepatic fibrosis" Proc. Natl Acad Sci USA. 1999; 96(22): 12719-24.
Ghiassi-Nejad et al, "Advances in Anti-Fibrotic Therapy" Expert Rev Gastroenteral Hepatol. 2008; 2(6) 803-16.
Goodman et al., "Extraction and Recombination Studies of the Interaction of Retinol with Human Plasma Retinol-Binding Protein." Journal of Lipid Research, vol. 13, 1972, pp. 338-347.
Inoue et al. "The role of monocyte chemoattractant protein-1 in experimental chronic pancreatitis model induced by dibutyltin dichloride in rats." Pancreas 2002; 25:e64-70.
Kakumitsu et al, "Transgenic mice overexpressing murine thrombopoietin develop myelofibrosis and osteoclerosis" Leukemia Research 29; 761-769, 2005.
Kamps, J.AAM. et al., "Massive targeting of liposomes, surface-modified with anionized albumins, to hepatic endothelial cells," Proceedings of the National Academy of Sciences USA 1997; 94(21):11681-11685.
Kang, et al. "Mannose- 6-Phosphateyinsuling-like growth factor-II receptor is a retinoic acid." Proc. Natl. Acad. Sci. vol. 95, pp. 13671-13676, Dec. 1998.
Kikuchi, H., Liposomes based on nanotechnology. Past, present and future. Part II, Pharm Tech Japan 2003; 19(3):419-433.
Kim et al., "Folate-tethered emulsion for the target delivery of retinoids to cancer cells." European Journal of Pharmaceutics and Biopharmaceutics. 68:618-625. (2008).
Li, D. et al., "Liver fibrogenesis and the role of hepatic stellate cells: New insights and prospects for therapy," Journal of Gastroenterology and Hepatology 1999; 14(7):618-633.
Liebecq, "Biochemical Nomenclature and Related Documents", 2nd Ed. Portland Press, pp. 247-251 (1992).
Lim et al., "Formulation parameters determining the physicochemical characteristics of solid lipid nanoparticles loaded with all-trans retinoic acid." International Journal of Pharmaceutics. 243:135-146. (2002).
Ma et al., "Comparison of Stability for All-trans Retinoic Acid Nanosuspensions and Lipid Nanoparticle Formulations." International Conference on Complex Medical Engineering. 197-202. (2007).
Marcucci et al., "Active targeting with particulate drug carriers in tumor therapy: fundamentals and recent progress." Drug Discovery Today. 9(5):219-228. (2004).

(56) References Cited

OTHER PUBLICATIONS

Nastruzzi et al., "Liposome-associated retinoic acid increased in vitro antiproliferative effects on neoplastic cells" FEBS Letters (1990) 259(2):293-296.

Singh, et al. "Liposome encapsulated vitamin a compounds exhibit greater stability and diminished toxicity." Biophysical Chemistry, vol. 73, pp. 155-162, 1998.

Socaciu, et al., Different Ways to Insert Carotenoids into Liposomes Affect Structure and Dynamics of the Bilayer Differently. Biophysical Chemistry, vol. 99, pp. 1-15, 2002.

Temming et al., "RGD-based strategies for selective delivery of therapeutics and imaging agents to the tumour vasculature" Drug Resist Updat. 2005; 8(6): 381-402.

Torchilin et al., "Immunomicelles: Targeted pharmaceutical carriers for poorly soluble drugs." PNAS. 100(10):6039-6044. (2003).

Torchilin, V. P. "Drug Targeting," European Journal of Pharmaceutical Sciences. (2000) 11(2):81-91.

Torchilin, VP., "Targeted pharmaceutical nanocarriers for cancer therapy and imaging" The AAPS Journal (2007) 9(2):E128-47.

Tsuji, H. et al., "Targeting of liposomes surface-modified with glycyrrhizin to the liver. I. Preparation and biological disposition," Chemical & Pharmaceutical Bulletin 1991; 39(4):1004-08.

Vogel et al., "An immortalized rat liver stellate cell line (HSC-TS): a new cell model for the study of retinoid metabolism in vitro." Journal of Lipid Research, vol. 41, 2000, pp. 882-893.

Wassail, S.R., et al. "Retinoid-Phospholipid Interactions As Studied by Magnetic Resonance" Bulletin of Magnetic Resonance, vol. 9 No. 3, pp. 85-89, 1987.

Weidenbach et al. "Failure of a Prolyl 4-Hydroxylase Inhibitor to Alter Extracellular Matrix Deposition during Experimental Pancreatitis" Digestion 1997; 58: 50-57.

Whitmer et al., Membrane-membrane interactions associated with rapid transfer of liposomal bilirubin to microsomal UDP-glucuronyltransferase. Biochemical Journal, vol. 244, pp. 41-47, 1987.

Williams et al. "Relaxin inhibits effective collagen deposition by cultured hepatic stellate cells and decreases rat liver fibrosis in vivo" Gut 2001; 49:577-583.

Wu, J. et al., "Modification of liposomes for liver targeting," Journal of Hepatology (1996)24(6):757-763.

Zhang et al., "Cationic lipids and polymers mediated vectors for delivery of siRNA," J. Control Release (2007) 123: 1-10.

Zhao et al.; "Tumor-selective targeted delivery of genes and antisense oligodeoxyribonucleotides via the folate receptor," Advanced Drug Delivery Reviews (2004) 56: 1193-1204.

Examination Report dated Nov. 11, 2015 for EP Application No. 11814740.4, filed Aug. 5, 201.

Liu et al., "Effects on the tyrosine protein kinase inhibitor genistein of the proliferation, activation of cultured rat hepatic stellate cells" *World J Gastroenterol* (2002) 8(4):739-745.

Marra et al., "Ligands of Peroxisome Proliferator-Activated Receptor g Modulate Profibrogneic and Proinflammatory Actions in Hepatic Stellate Cells" *Gastroenterology* (2000) 119(2):466-478.

Qi et al., "Blockade of type to transforming growth factor signaling prevents liver fibrosis and dysfunction in the rat" *Proc. Natl Acad. Sci. USA* (1999) 96(5):2345-2349.

Yoshiji et al., "Angiotensin-II Type 1 Receptor Interaction is a Major Regulator for Liver Fibrosis Development in Rats" *Hepatology* (2001) 34(4):745-750.

Office Action dated Oct. 6, 2015 for Taiwanese Application No. 100127765, filed Aug. 4, 2011.

Office Action dated Aug. 11, 2015 for Chinese Application No. 201180038574.2, filed Aug. 5, 2011.

Office Action dated Mar. 29, 2015 for Russian Application No. 2013109370/10(013917), filed Aug. 5, 2015.

Office Action dated Dec. 25, 2015 in Russian Application No. 2013109370/10(013917).

Office Action mailed Jan. 29, 2016 in Japanese Patent Application No. 2015-001283.

Office Action dated Apr. 6, 2016 in Chinese Application 201180038574.2.

* cited by examiner

TRANSPLANTATION OF HEPATIC STEM CELLS TO BILE DUCT LIGATION RAT AND TREATMENT USING VA-lip siRNAgp46

α-SMA STAINING

FIG. 3

TREATMENT USING VA-lip siRNAgp46 OF BDL RAT TO WHICH GFP-tg RAT-DERIVED HEPATIC STEM CELLS HAD BEEN TRANSPLANTED

Animal: BDL rats (One to which hepatic stem cells separated from GFP-tg rat had been transplanted)
siRNA: siRNAgp46, siRNAscramble
Number of administrations of siRNA: 12 times

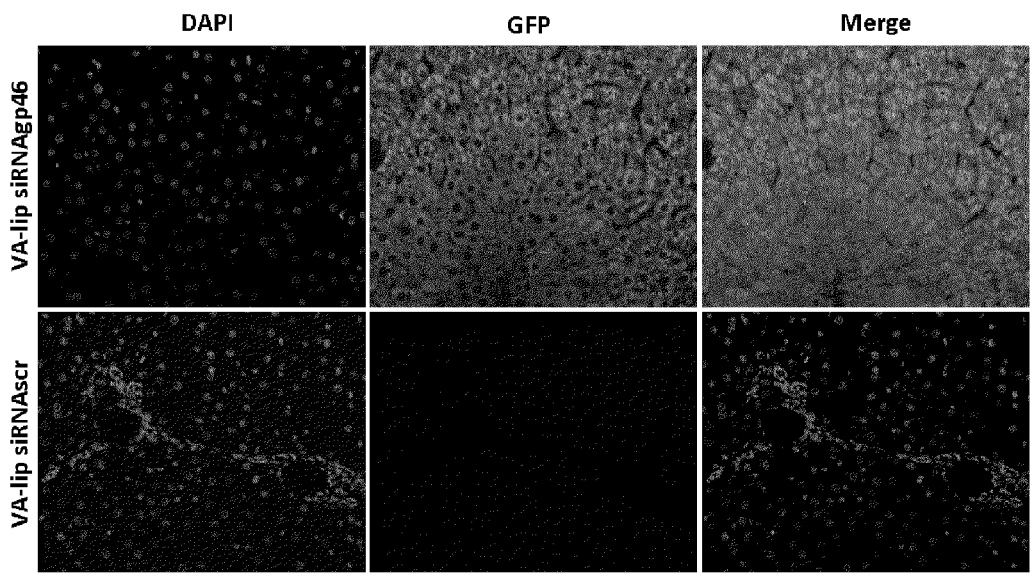

FIG. 4

TRANSPLANTATION OF HEPATIC STEM CELLS TO BILE DUCT LIGATION RAT AND TREATMENT USING VA-lip siRNAgp46

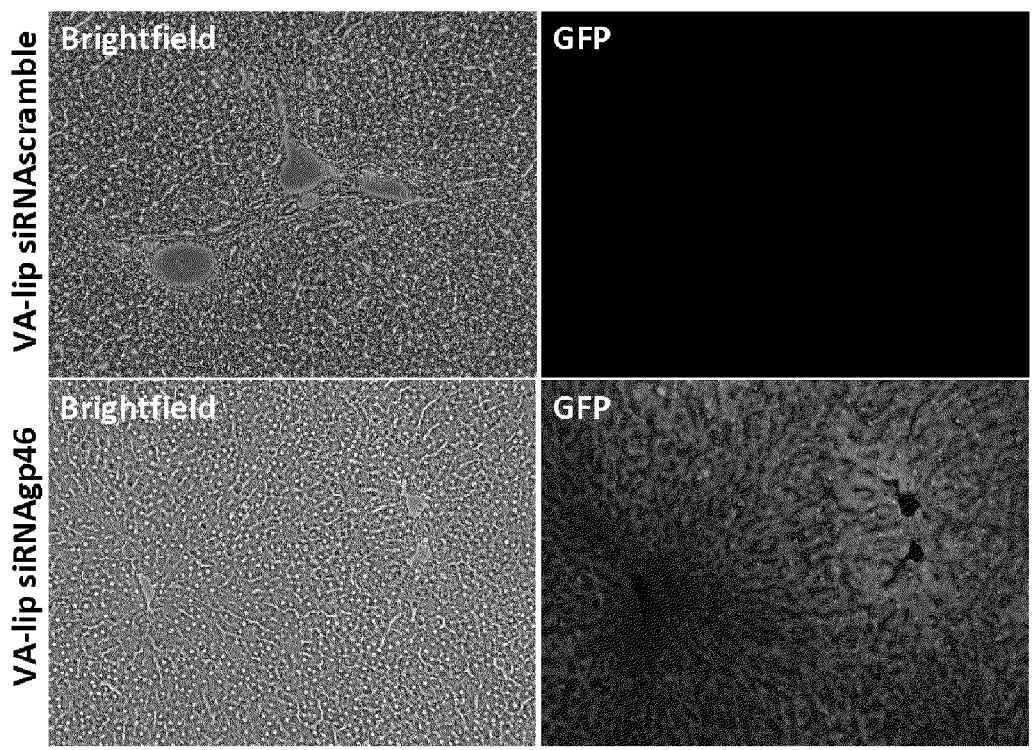

TREATMENT USING VA-lip siRNAgp46 OF BDL RAT TO WHICH GFP-tg RAT-DERIVED HEPATIC STEM CELLS HAD BEEN TRANSPLANTED
VA-lip siRNAgp46 (×200) Cell transplantation site: GFAP (Quiescent HSCs marker)

TREATMENT USING VA-lip siRNAgp46 OF BDL RAT TO WHICH GFP-tg RAT-DERIVED HEPATIC STEM CELLS HAD BEEN TRANSPLANTED TREATMENT USING VA-lip siRNAgp46 OF BDL RAT TO WHICH GFP-tg RAT-DERIVED HEPATIC STEM CELLS HAD BEEN TRANSPLANTED
VA-lip siRNAgp46 (×200) Cell transplantation site: α-SMA (Activated HSCs marker)

TREATMENT USING VA-lip siRNAgp46 OF BDL RAT TO WHICH GFP-tg RAT-DERIVED HEPATIC STEM CELLS HAD BEEN TRANSPLANTED
VA-lip siRNAgp46 (×200) Cell transplantation site : Albumin (Hepatocyte marker)

TREATMENT USING VA-lip siRNAgp46 OF BDL RAT TO WHICH GFP-tg RAT-DERIVED HEPATIC STEM CELLS HAD BEEN TRANSPLANTED
VA-lip siRNAgp46 (×200) Cell transplantation site: CK19 (Bile duct epithelial cell marker)

TREATMENT USING VA-lip siRNAgp46 OF BDL RAT TO WHICH GFP-tg RAT-DERIVED HEPATIC
STEM CELLS HAD BEEN TRANSPLANTED VA-lip siRNAgp46 (×200) Cell transplantation site: ve-CAD (Blood Vessel endothelial cell marker)

TREATMENT USING VA-lip siRNAgp46 OF BDL RAT TO WHICH GFP-tg RAT-DERIVED HEPATIC STEM CELLS HAD BEEN TRANSPLANTED VA-lip siRNAgp46 (×400) Cell transplantation site: ve-CAD (Blood Vessel endothelial cell marker)

TREATMENT USING VA-lip siRNAgp46 OF BDL RAT TO WHICH GFP-tg RAT-DERIVED HEPATIC STEM CELLS HAD BEEN TRANSPLANTED VA-lip siRNAgp46 (×200) Region other than cell transplantation site FIG. 13
A
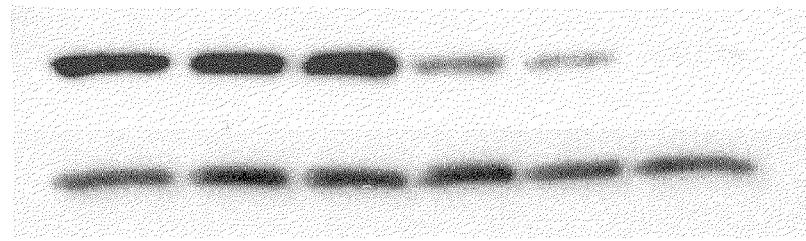
B
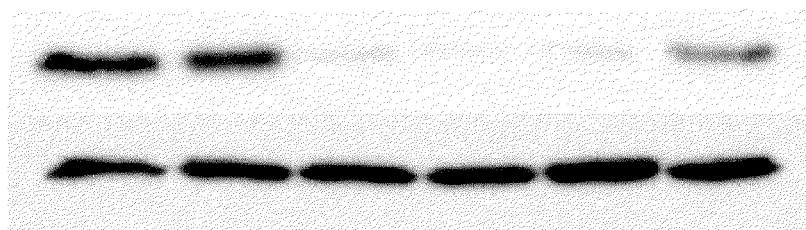

FIG. 16
A
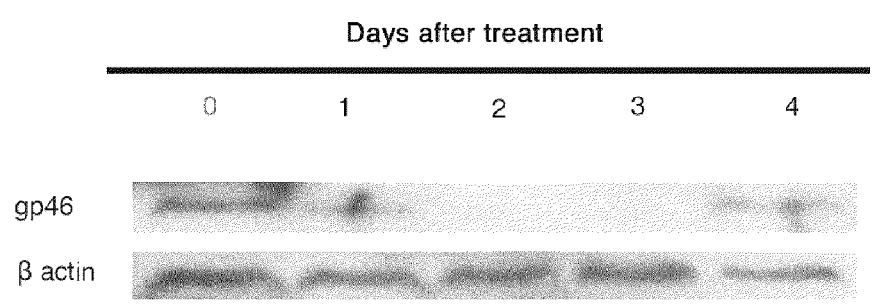
B
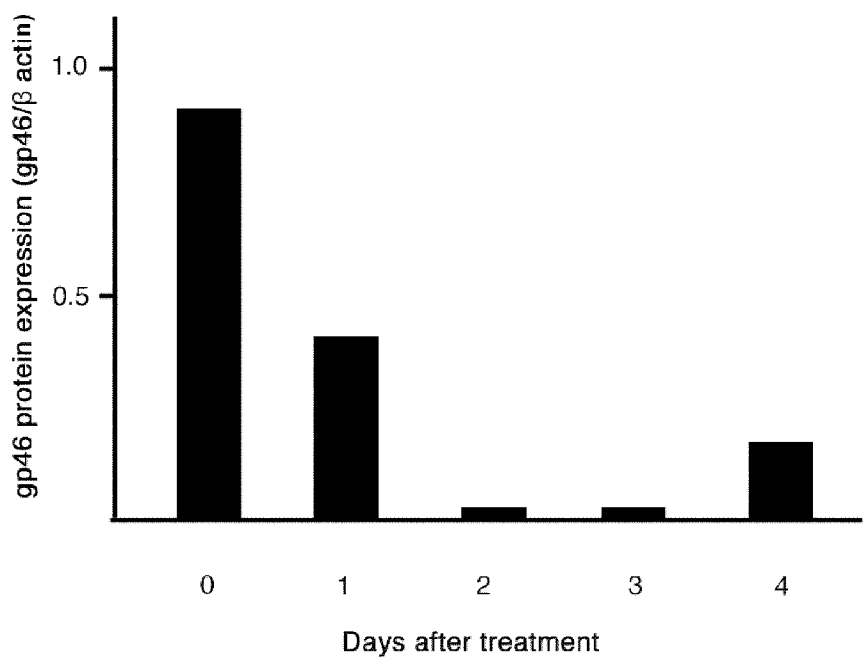

SEQUENCE LISTING

```
<160> NUMBER OF SEQ ID NOS: 4

<210> SEQ ID NO 1
<211> LENGTH: 27
<212> TYPE: RNA
<213> ORGANISM: Artificial sequence
<220> FEATURE:
<223> OTHER INFORMATION: gp46 siRNA sense strand

<400> SEQUENCE: 1
guuccaccau aagaugguag acaacag                                         27

<210> SEQ ID NO 2
<211> LENGTH: 27
<212> TYPE: RNA
<213> ORGANISM: Artificial sequence
<220> FEATURE:
<223> OTHER INFORMATION: gp46 siRNA antisense strand

<400> SEQUENCE: 2
guugucuacc aucuuauggu ggaacau                                         27

<210> SEQ ID NO 3
<211> LENGTH: 27
<212> TYPE: RNA
<213> ORGANISM: Artificial sequence
<220> FEATURE:
<223> OTHER INFORMATION: siRNArandom sense strand

<400> SEQUENCE: 3
cgauucgcua gaccggcuuc auugcag                                         27
```

-continued

```
<210> SEQ ID NO 4
<211> LENGTH: 27
<212> TYPE: RNA
<213> ORGANISM: Artificial sequence
<220> FEATURE:
<223> OTHER INFORMATION: siRNArandom antisense strand

<400> SEQUENCE: 4
gcaaugaagc cggucuagcg aaucgau                                           27
```

COMPOSITION FOR REGENERATING NORMAL TISSUE FROM FIBROTIC TISSUE

TECHNICAL FIELD

The present invention relates to a composition and method for regenerating normal tissue from fibrotic tissue.

BACKGROUND ART

Fibrosis of tissue is caused by the excessive production and accumulation in tissue of extracellular matrix, which is mainly collagen. When tissue is damaged by a stimulus such as oxidative stress, hypoxia, inflammation, or apoptosis, damaged tissue is repaired by replacement with extracellular matrix, but in the case of the damage being serious or in the case of such stimulation becoming chronic, the accumulation of extracellular matrix becomes excessive, and the tissue cannot perform its function sufficiently. Fibrosis is seen in various types of organs, such as the liver, pancreas, lung, kidney, bone marrow, and heart, and it is thought that collagen-producing cells such as myofibroblasts are related to a disease state. Conventionally, it is though that fibrosis is an irreversible phenomenon and that once tissue has become fibrotic it does not return to its original state, but recently, there have been some reports suggesting that fibrosis is reversible, and that when the above-mentioned fibrotic stimulus disappears, the extracellular matrix accumulated in the tissue decreases (see Non-Patent Documents 1 to 3).

However, there have been no detailed reports regarding what is specifically happening in the tissue after pathological accumulation of extracellular matrix decreases, and it has been completely unknown until now for regeneration of normal tissue to occur in such fibrotic tissue or for regeneration of normal tissue to be possible.

Furthermore, the fibrosis of tissue not only includes fibroses for which the cause of the disease is clear and can be removed, such as fibrosis derived from viral infection, drinking alcohol, drugs, etc., but also includes fibroses for which the direct cause of the disease is unclear, such as for example cryptogenic cirrhosis, idiopathic pulmonary fibrosis, or idiopathic myelofibrosis, and those for which the direct cause of the disease is known but the origin of the cause of the disease is unclear or is difficult to remove, such as for example primary biliary cirrhosis, nonalcoholic steatohepatitis (NASH)-derived hepatic fibrosis, and primary sclerosing cholangitis. Tissue with the presence of such fibrosis, for which it is difficult to remove the cause of the disease, is in a state in which it is always exposed to a fibrotic stimulus, but it has been completely unknown until now that the pathological accumulation of extracellular matrix in such fibrotic tissue can be reduced, and certainly not known that the tissue can be regenerated.

PRIOR ART DOCUMENTS

Non-Patent Documents

[Non-Patent Document 1] Issa et al., Gastroenterology. 2004; 126(7): 1795-808
[Non-Patent Document 2] Iredale, J Clin Invest. 2007; 117 (3): 539-48
[Non-Patent Document 3] Sato et al., Nat Biotechnol. 2008; 26(4): 431-42

SUMMARY OF THE INVENTION

Problems to be Solved by the Invention

It is an object of the present invention to provide a composition and method for therapeutically regenerating normal tissue in tissue in which fibrosis is present.

Means for Solving the Problems

While carrying out an intensive investigation in order to solve the above-mentioned problems, the present inventors have found that even in fibrotic tissue that continually receives a fibrotic stimulus, collagen accumulated in the tissue can be reduced and, furthermore, normal tissue can be regenerated from the fibrotic tissue by removing the collagen accumulated in the tissue and ensuring there is space in which stem cells can grow and differentiate, and the present invention has thus been accomplished. As described above, although it is known that when a fibrotic stimulus disappears extracellular matrix accumulated in the tissue can decrease, it has been completely unknown until now that in fibrotic tissue that continually receives a fibrotic stimulus collagen accumulated in the tissue can be reduced and that normal tissue can be regenerated from fibrotic tissue by actively removing collagen accumulated in the tissue, and these are surprising findings.

Therefore, the present invention relates to the following.
(1) A pharmaceutical composition for regenerating normal tissue from fibrotic tissue, the composition containing a collagen-reducing substance.
(2) The pharmaceutical composition according to (1) above, wherein the collagen-reducing substance is selected from the group consisting of a suppressor of collagen production by collagen-producing cells, a promoter of collagen decomposition, and a suppressor of a collagen decomposition inhibitor.
(3) The pharmaceutical composition according to (1) or (2) above, wherein it further contains a targeting agent for collagen-producing cells in fibrotic tissue.
(4) The pharmaceutical composition according to (3) above, wherein the targeting agent is a retinoid.
(5) The pharmaceutical composition according to any one of (1) to (4) above, wherein the fibrotic tissue continually receives a fibrotic stimulus.
(6) The pharmaceutical composition according to any one of (1) to (5) above, wherein it is for regenerating fibrotic tissue in a space for the growth and differentiation of stem cells, the space being formed by a reduction of collagen accumulated in the fibrotic tissue.
(7) The pharmaceutical composition according to any one of (2) to (6) above, wherein the suppressor of collagen production by collagen-producing cells is selected from the group consisting of a TGFβ inhibitor, HGF or a substance promoting the production thereof, a PPARγ ligand, an angiotensin inhibitor, a PDGF inhibitor, relaxin or a substance promoting the production thereof, a substance that inhibits the production and secretion of an extracellular matrix component, a cell activity supressor, a cell growth supressor, and an apoptosis-inducing substance.
(8) The pharmaceutical composition according to any one of (2) to (6) above, wherein the promoter of collagen decomposition is collagenase or a collagenase production promoter.
(9) The pharmaceutical composition according to any one of (2) to (6) above, wherein the suppressor of a collagen decomposition inhibitor is a TIMP inhibitor.

Effects of the Invention

In accordance with the present invention, it has become clear that normal tissue can be regenerated from fibrotic tissue, the regeneration of normal tissue therefrom having been thought not to occur until now. This enables normal tissue to be therapeutically regenerated from fibrotic tissue, and a new regenerative therapy for a fibrotic disease becomes possible.

Furthermore, in accordance with the present invention, it becomes possible to treat fibrotic tissue that is continually exposed to a fibrotic stimulus, and since a medical treatment is realized for all types of fibrotic diseases including a fibrotic disease for which there is no conventional effective therapy and a fibrotic disease for which there is only a treatment involving organ transplantation, an enormous contribution to medical and veterinary treatment can be anticipated.

BRIEF DESCRIPTION OF DRAWINGS

FIG. 3 is a fluorescence image showing the localization of DAPI and GFP at hepatic stem cell transplantation sites.

FIG. 4 shows bright field images and GFP fluorescence images of hepatic stem cell transplantation sites.

FIG. 5 B is a photographic diagram comparing DAPI and GFP fluorescence images and an image fluorescently stained by a GFAP antibody in a VA-lip siRNAgp46-treated group (400× magnification).

FIG. 9 B is a photographic diagram comparing DAPI and GFP fluorescence images and an image fluorescently stained by a ve-CAD antibody in a VA-lip siRNAgp46-treated group (400× magnification).

FIG. 13 is a Western blot image showing the suppression of the expression of gp46 in rat pancreatic stellate cells by siRNAgp46. A shows the difference in suppression effect according to VA-lip siRNAgp46 concentration, and B shows the duration of suppression effect.

FIG. 16 is a diagram showing the expression of gp46 protein in the pancreas 0, 1, 2, 3, and 4 days after VA-lip siRNAgp46 administration of rats to which VA-lip siRNAgp46 (siRNA 0.75 mg/kg) was administered on the 14th day after treatment with DBTC. A shows the result of Western blotting of pancreatic cell debris, and B shows the result of a quantitative concentration analysis using β-actin for normalization.

MODES FOR CARRYING OUT THE INVENTION

Figure 1:
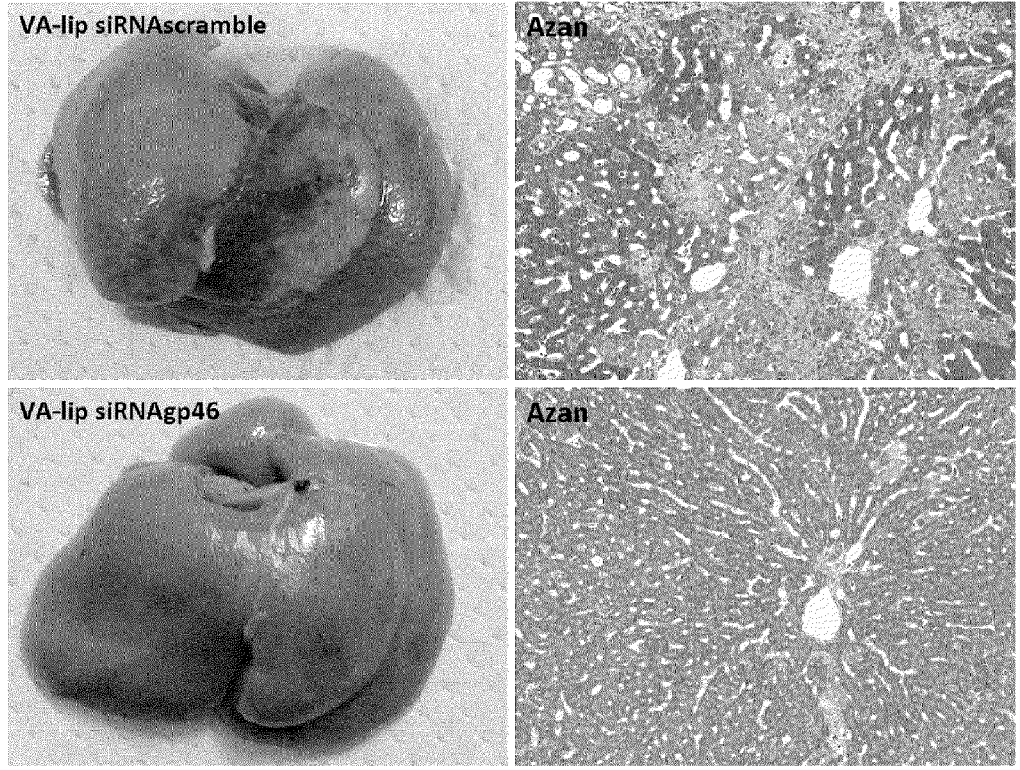
FIG. 1 is a photographic diagram showing the overall appearance of livers harvested from test rats and Azan-stained images of representative sections thereof.

The present invention relates to a composition, containing a collagen-reducing substance, for regenerating normal tissue from fibrotic tissue.

In the present invention, a 'collagen-reducing substance' means any substance that can reduce the amount of collagen accumulated in tissue. Although it is not intended to be bound by a specific theory, since one of the causes for the accumulation of collagen in fibrotic tissue is thought to be a shift in the balance between production and decomposition of collagen to the production side, the collagen-reducing substance can include not only a suppressor of collagen production, but also a collagen decomposition promoter and a suppressor of an inhibitor of a collagen decomposition promoter. Therefore, examples of the collagen-reducing substance include, but are not limited to, a suppressor of collagen production by collagen-producing cells, a promoter of collagen decomposition, and a suppressor of a collagen decomposition inhibitor. Although there is no particular limitation, the collagen in the present invention is preferably a collagen involved in fibrosis such as for example type I, III, or V collagen, and particularly preferably type I collagen, which is present in fibrotic tissue in the largest amount.

In the present invention, the collagen-producing cells mean any cells that produce collagen in fibrotic tissue, and examples include, but are not limited to, activated stellate cells and myofibroblasts. It is thought that activated stellate cells and myofibroblasts are the main collagen-producing sources in fibrotic tissue, and they are characterized by the expression of α-SMA (α-smooth muscle actin). Therefore, the activated stellate cells and myofibroblasts in the present invention are identified by means of immunostaining, etc. using an anti-α-SMA antibody that is detectably labeled.

The suppressor of collagen production by collagen-producing cells includes any drug that directly or indirectly suppresses the physical, chemical, and/or physiological actions, etc. of same cells involved in collagen accumulation in fibrotic tissue, and examples thereof include, but are not limited to, a TGFβ (Transforming growth factor-beta) inhibitor, HGF (Hepatocyte growth factor) or a substance promoting the production thereof, a PPARγ (Peroxisome proliferator-activated receptor gamma) ligand, an angiotensin inhibitor, a PDGF (Platelet-derived growth factor) inhibitor, relaxin or a substance promoting the production thereof, a substance that inhibits the production and secretion of an extracellular matrix component, a cell activity suppressor, a cell growth suppressor, and an apoptosis-inducing substance.

Examples of the TGFβ inhibitor include, but are not limited to, a truncated TGFβ type II receptor (Qi et al., Proc Natl Acad Sci USA. 1999; 96 (5): 2345-9), a soluble TGFβ type II receptor (George et al., Proc Natl Acad Sci USA. 1999; 96 (22): 12719-24), a TGFβ activity inhibitor such as an anti-TGFβ antibody, a TGFβ production inhibitor such as an RNAi molecule, ribozyme, or antisense nucleic acid complementary to TGFβ, vectors expressing these, and cells transformed thereby. In one embodiment of the present invention, the TGFβ inhibitor inhibits the activity and/or production of TGFβ1.

Examples of substances promoting the production of HGF or relaxin include, but are not limited to, a nucleic acid coding for HGF or relaxin, an expression construct containing this, expression vectors containing these, and cells transformed thereby.

Examples of the PPARγ ligand include, but are not limited to, an endogenous ligand such as 15-deoxy-Δ12,14-prostaglandin J2, nitrolinoleic acid, oxidized LDL (Low density lipoprotein), a long chain fatty acid, or an eicosanoid, and an exogenous ligand such as a thiazolidinedione medicinal agent such as troglitazone, pioglitazone, rosiglitazone, balaglitazone or rivoglitazone, or a non-steroidal anti-inflammatory drug.

Examples of the angiotensin inhibitor include, but are not limited to, an angiotensin receptor antagonist such as telmisartan, losartan, valsartan, candesartan cilexetil, olmesartan medoxomil, or irbesartan. The angiotensin includes angiotensins I, II, III, and IV. Furthermore, examples of the angiotensin receptor include, but are not limited to, an angiotensin type 1 receptor (AT1).

Examples of the PDGF inhibitor include, but are not limited to, a PDGF activity inhibitor such as an anti-PDGF antibody, a PDGF production inhibitor such as an RNAi molecule, ribozyme, or antisense nucleic acid complementary to PDGF, vectors expressing these, and cells transformed thereby.

Examples of the substance that inhibits the production and secretion of an extracellular matrix component include, but are not limited to, a substance, such as an RNAi molecule, a ribozyme, or an antisense nucleic acid, that suppresses the expression of an extracellular matrix component such as collagen, proteoglycan, tenascin, fibronectin, thrombospondin, osteopontin, osteonectin, or elastin, a substance having a dominant negative effect such as a dominant negative mutant, vectors expressing these, and cells transformed thereby. Examples of drugs that inhibit the production and secretion of collagen include, but are not limited to, inhibitors of HSP (Heat shock protein) 47, which is a collagen-specific molecular chaperone essential for intracellular transport and molecular maturation common to the synthetic processes for various types of collagen, for example HSP47 expression inhibitors such as an RNAi molecule, ribozyme, or antisense nucleic acid complementary to HSP47, a substance having a dominant negative effect such as an HSP47 dominant negative mutant, vectors expressing these, and cells transformed thereby.

Examples of the cell growth suppressor include, but are not limited to, an alkylating agent (e.g. ifosfamide, nimustine, cyclophosphamide, dacarbazine, melphalan, ranimustine, etc.), an antitumor antibiotic (e.g. idarubicin, epirubicin, daunorubicin, doxorubicin, pirarubicin, bleomycin, peplomycin, mitoxantrone, mitomycin C, etc.), a metabolism antagonist (e.g. gemcitabine, enocitabine, cytarabine, tegafur-uracil, tegafur-gimeracil-oteracil potassium combination drug, doxifluridine, hydroxycarbamide, fluorouracil, methotrexate, mercaptopurine, etc.), an alkaloid such as etoposide, irinotecan, vinorelbine, docetaxel, paclitaxel, vincristine, vindesine, or vinblastine, a platinum complex such as carboplatin, cisplatin, or nedaplatin, and a statin such as lovastatin or simvastatin.

Examples of the cell activity suppressor include, but are not limited to, a sodium channel inhibitor.

Examples of the apoptosis-inducing agent include, but are not limited to, compound 861, gliotoxin, and atorvastatin.

Examples of the promoter of collagen decomposition include, but are not limited to, various types of collagenase and a substance promoting the production thereof. Examples of the collagenase include, but are not limited to, the MMP family, such as MMP (Matrix metalloproteinase) 1, 2, 3, 9, 13, and 14. Examples of the collagenase production promoter include, but are not limited to, a nucleic acid coding for the collagenase, an expression construct containing this, expression vectors containing these, and cells transformed thereby.

Examples of the inhibitor of a collagen decomposition promoter include, but are not limited to, TIMP (Tissue inhibitor of metalloproteinase, TIMP1 and TIMP2, etc.). Therefore, examples of the suppressor of the above inhibitor include, but are not limited to, a TIMP activity inhibitor such as an antibody for TIMP, a TIMP production inhibitor such as an RNAi molecule, ribozyme, or antisense nucleic acid complementary to TIMP, vectors expressing these, and cells transformed thereby.

The RNAi molecule in the present invention includes RNA such as siRNA (small interfering RNA), miRNA (micro RNA), shRNA (short hairpin RNA), ddRNA (DNA-directed RNA), piRNA (Piwi-interacting RNA), rasiRNA (repeat associated siRNA), and modifications of these. Furthermore, the nucleic acid in the present invention includes RNA, DNA, PNA, and composites thereof.

In the present invention, 'fibrotic tissue' means tissue in which extracellular matrix, mainly collagen, has accumulated in an amount greater than normal. In addition to collagen, examples of the extracellular matrix include, but are not limited to, proteoglycan, tenascin, fibronectin, thrombospondin, osteopontin, osteonectin, and elastin. The amount of collagen accumulated in tissue may be quantified for example by using the amount of hydroxyproline in the tissue as an indicator or by subjecting the tissue to collagen staining (e.g. Masson trichrome staining, Azan staining, sirius red staining, Elastica van Gieson staining, etc.) and carrying out an image analysis. The amount of extracellular matrix in fibrotic tissue in the present invention may be at least 5%, at least 10%, at least 25%, at least 50%, at least 100%, at least 200%, at least 300%, at least 400%, or at least 500% compared with that of normal tissue. Since it is thought that the production of collagen by activated stellate cells and/or myofibroblasts contributes to fibrosis of tissue, the fibrotic tissue in the present invention typically contains activated stellate cells and/or myofibroblasts. The fibrotic tissue may be any tissue in the body as long as it has the above-mentioned features, and examples thereof include, but are not limited to, the liver, the pancreas, the lung, the kidney, the bone marrow, the vocal cord, the larynx, the mouth cavity, the heart, the spleen, the mediastinum, the retroperitoneum, the uterus, the skin, the mammary gland, and the intestinal tract.

Therefore, the fibrotic tissue may be an affected area in various organ fibroses. Examples of the organ fibroses include, but are not limited to, hepatic fibrosis, hepatic cirrhosis, vocal cord scar formation, vocal cord mucosal fibrosis, laryngeal fibrosis, pulmonary fibrosis, pancreatic fibrosis, myelofibrosis, myocardial infarction, fibrosis of the myocardium following myocardial infarction, myocardial fibrosis, endomyocardial fibrosis, splenic fibrosis, mediastinal fibrosis, lingual submucous fibrosis, intestinal fibrosis (e.g. that associated with an inflammatory bowel disease, etc.), retroperitoneal fibrosis, uterine fibrosis, scleroderma, and a fibrous disease of the breast.

The hepatic fibrosis and hepatic cirrhosis in the present invention include not only those caused by a viral infection with hepatitis B or C virus, drinking alcohol, fatty liver, a parasitic infection, a congenital metabolic abnormality, a hepatotoxic substance, etc., but also those for which the cause is not specified. Therefore, examples of the hepatic cirrhosis in the present invention include, but are not limited to, Charcot's cirrhosis, Todd's cirrhosis, primary biliary cirrhosis, unilobar cirrhosis, secondary biliary cirrhosis, obstructive cirrhosis, cholangiolitic cirrhosis, biliary cirrhosis, atrophic cirrhosis, nutritional cirrhosis, postnecrotic cirrhosis, posthepatitic cirrhosis, nodular cirrhosis, mixed cirrhosis, micronodular cirrhosis, compensated cirrhosis, macronodular cirrhosis, septal cirrhosis, cryptogenic cirrhosis, decompensated cirrhosis, periportal cirrhosis, portal cirrhosis, and alcoholic cirrhosis.

The pulmonary fibrosis in the present invention includes not only pulmonary fibrosis in a strict sense but also pulmonary fibrosis in a broad sense, including coexistence with interstitial pneumonia. The pulmonary fibrosis in the present invention can be caused by any interstitial pneumonia such as for example infectious interstitial pneumonia associated with viral pneumonia, fungal pneumonia, mycoplasma pneumonia, etc., interstitial pneumonia associated with a collagen disease such as rheumatoid arthritis, systemic scleroderma, dermatomyositis, polymyositis, a mixed connective tissue disease (MCTD, Mixed connective tissue disease), interstitial pneumonia associated with radiation exposure, interstitial pneumonia induced by a drug such as an anticancer agent such as bleomycin, a Chinese herbal medicine such as Sho-saiko-to, interferon, an antibiotic, or Paraquat, or idiopathic interstitial pneumonia such as idiopathic pulmonary fibrosis, nonspecific interstitial pneumonia, acute interstitial pneumonia, cryptogenic organizing pneumonia, a respiratory bronchiolitis-associated interstitial lung disease, desquamating interstitial pneumonia, or lymphocytic interstitial pneumonia, and the pulmonary fibrosis in the present invention therefore includes those in which the above interstitial pneumonia has become chronic.

The myelofibrosis in the present invention includes not only primary myelofibrosis but also secondary myelofibrosis. Examples of the secondary myelofibrosis include, but are not limited to, those that are secondary to a disease such as acute myeloid leukemia, acute lymphoblastic leukemia, chronic myeloid leukemia, polycythemia vera, primary thrombocythemia, myelodysplastic syndrome, multiple myeloma, malignant lymphoma, carcinoma, systemic lupus erythematosus, or progressive systemic sclerosis, or to radiation exposure.

Renal fibrosis in the present invention can be caused by any interstitial nephritis such as for example infectious interstitial nephritis associated with streptococcal nephritis, staphylococcal nephritis, pneumococcal nephritis, viral nephritis associated with varicella, hepatitis B, hepatitis C, HIV, etc., nephritis due to a parasitic infection such as malaria, fungal nephritis, mycoplasma nephritis, etc., interstitial nephritis associated with a collagen disease such as systemic lupus erythematosus (lupus nephritis), systemic scleroderma (collagen disease of the kidney), or Sjogren syndrome, nephritis associated with a blood vessel immune disease such as purpura nephritis, polyarteritis, rapidly progressive glomerulonephritis, etc., interstitial nephritis associated with radiation exposure, interstitial nephritis induced by a drug such as a gold drug, an NSAID, penicillamine, an anticancer agent such as bleomycin, an antibiotic, or Paraquat, etc., an allergic nephritis due to an insect bite, pollen, or an Anacardiaceae family plant, amyloidosis nephritis, diabetic nephropathy, chronic glomerulonephritis, nephritis associated with malignant nephrosclerosis or a polycystic kidney disease, tubulointerstitial nephritis, nephritis associated with gestational toxicosis or a cancer, membranoproliferative glomerulonephritis, IgA nephropathy nephritis, mixed cryoglobulinemic nephritis, Goodpasture's syndrome nephritis, Wegener's granulomatous nephritis, or an idiopathic interstitial nephritis such as acute interstitial nephritis, etc., and the renal fibrosis in the present invention therefore includes those in which the above interstitial nephritis has become chronic.

In one embodiment of the present invention, the fibrotic tissue is that which continually receives a fibrotic stimulus. In the present invention, the fibrotic stimulus means any stimulus that induces fibrosis, and examples include, but are not limited to, oxidative stress, hypoxia, inflammation, and apoptosis (see Ghiassi-Nejad et al., Expert Rev Gastroenterol Hepatol. 2008; 2(6): 803-16). Examples of such tissue include fibrotic tissue that is experiencing chronic inflammation and tissue that is continuously exposed to a cytotoxic substance (e.g. liver tissue in which cholestasis is caused by a bile duct disease, etc.). Furthermore, such tissue also includes tissue affected by fibrosis for which the direct cause of the disease is unclear, such as for example cryptogenic cirrhosis, idiopathic pulmonary fibrosis, or idiopathic myelofibrosis, etc., or affected by those for which the direct cause of the disease is known but the origin of the cause of the disease is unclear or it is difficult to remove, such as for example primary biliary cirrhosis, nonalcoholic steatohepatitis (NASH)-derived hepatic fibrosis, primary sclerosing cholangitis, idiopathic pulmonary fibrosis, idiopathic interstitial pneumonia-derived pulmonary fibrosis, primary myelofibrosis, idiopathic interstitial nephritis-derived renal fibrosis, inflammatory bowel disease (e.g. Crohn's disease, ulcerative colitis, etc.), or systemic scleroderma, etc.

In the present invention, 'regenerating normal tissue from fibrotic tissue' means recovering the tissue that has been denatured due to fibrosis at least to a state in which the fibrosis is of a lesser degree. That is, as fibrosis progresses, tissue is replaced by fibrous tissue, which is mainly extracellular matrix, and the regeneration of normal tissue from fibrotic tissue in the present invention is to reverse the above flow and replace the proliferated fibrous tissue with the original normal tissue. Therefore, the regeneration of normal tissue from fibrotic tissue in the present invention includes not only completely recovering fibrotic tissue to the original state but also partially recovering fibrotic tissue to the original state. The degree of regeneration of normal tissue may be evaluated by a histological examination of a biopsy sample, etc. based on normalization of the tissue structure, reduction in the region occupied by fibrous tissue, increase in the region occupied by normal tissue, etc., or when an abnormality of a biochemical index due to fibrosis is observed before treatment with the present composition, evaluation may be carried out based on improvement of the index, etc.

In one embodiment of the present invention, regeneration of normal tissue may be carried out by growth and differentiation of stem cells in a space that is formed due to reduction of collagen accumulated in fibrotic tissue. Therefore, one embodiment of the present invention relates to the pharmaceutical composition wherein it is for regenerating fibrotic tissue in a space for the growth and differentiation of stem cells, the space being formed by a reduction of collagen accumulated in the fibrotic tissue. Here, examples of the stem cells include, but are not limited to, those that are originally present in the tissue that has become fibrotic (hepatic stem cells, pancreatic stem cells, lung stem cells, renal stem cells, bone marrow stem cells, heart stem cells, spleen stem cells, uterine stem cells, skin stem cells, mammary stem cells, intestinal stem cells, mesenchymal stem cells, etc.), those that have moved from another place in the body and, furthermore, those that have been therapeutically administered. Moreover, the 'space' includes not only a cavity within the tissue but also a space with room in which cells can enlarge and grow such as for example a space in which the pressure between cells is decreased or a space having flexibility.

In one embodiment, the composition of the present invention further contains a targeting agent for collagen-producing cells in fibrotic tissue. By containing the targeting agent, it becomes possible to specifically deliver to collagen-producing cells, which are target cells, a collagen-reducing substance that is targeted to collagen-producing cells such as, for example, without limitation, a substance that inhibits the production and secretion of an extracellular matrix component, HGF or a substance promoting the production thereof, MMP or a substance promoting the production thereof, a TIMP inhibitor, a TGFβ production inhibitor, relaxin or a substance promoting the production thereof, etc., thereby enhancing the effect of the collagen-reducing substance used.

In one embodiment of the present invention, the targeting agent for collagen-producing cells is a retinoid. Although the mechanism in which targeting is carried out by means of a retinoid has not yet been clarified, it is surmised for example that a retinoid bound specifically to an RBP (retinol binding protein) is incorporated into a collagen-producing cell in fibrotic tissue via a certain type of receptor positioned on the surface of the cell. The ability of a retinoid to function as a targeting agent for collagen-producing cells is described in WO 2006/068232, JP, A, 2009-221164, JP, A, 2010-59124, etc.

A retinoid is one member of a group of compounds having a skeleton in which four isoprenoid units are connected in a head-to-tail manner (see G. P. Moss, "Biochemical Nomenclature and Related Documents", 2nd Ed. Portland Press, pp. 247-251 (1992)), and vitamin A is a generic descriptor for a retinoid qualitatively showing the biological activity of retinol. Examples of the retinoid that can be used in the present invention include, but are not particularly limited to, retinol (including all-trans retinol), retinal, retinoic acid (including tretinoin), an ester of retinol and a fatty acid, an ester of an aliphatic alcohol and retinoic acid, a retinoid derivative such as etretinate, isotretinoin, adapalene, acitretin, tazarotene, or retinyl palmitate, and a vitamin A analog such as fenretinide (4-HPR) or bexarotene.

Among them, retinol, retinal, retinoic acid, an ester of retinol and a fatty acid (e.g. retinyl acetate, retinyl palmitate, retinyl stearate, and retinyl laurate, etc.), and an ester of an aliphatic alcohol and retinoic acid (e.g. ethyl retinoate, etc.) are preferable in terms of efficiency of specific delivery of a substance to collagen-producing cells in fibrotic tissue.

All isomers, including cis/trans retinoids, are included in the scope of the present invention. A retinoid can be substituted with one or more substituents. The retinoid in the present invention includes not only one in an isolated state as well as a retinoid in a state in which it is dissolved or mixed in a medium that can dissolve or retain same.

The above-mentioned embodiment of the composition of the present invention may be formed only from a collagen-reducing substance targeted to collagen-producing cells as an active ingredient and a retinoid as a targeting agent, or may contain a carrier-constituting component other than the above. The carrier-constituting component in the present embodiment is not particularly limited; any component that is known in the medicinal and/or pharmaceutical fields may be used, but one for which at least inclusion of a retinoid or binding thereto is possible is preferable.

Examples of such a component include, but are not limited to, a lipid, for example, a phospholipid such as a glycerophospholipid, a sphingolipid such as sphingomyelin, a sterol such as cholesterol, a plant oil such as soybean oil or poppy seed oil, a mineral oil, a lecithin such as egg yolk lecithin, and a polymer. Among them, one that can form a liposome, such as for example a natural phospholipid such as lecithin, a semi-synthetic phospholipid such as dimyristoylphosphatidylcholine (DMPC), dipalmitoylphosphatidylcholine (DPPC), or distearoylphosphatidylcholine (DSPC), dioleylphosphatidylethanolamine (DOPE), dilauroylphosphatidylcholine (DLPC), or cholesterol is preferable.

A component that can avoid capture by the reticuloendothelial system is particularly preferred, and examples thereof include cationic lipids such as N-($\alpha$-trimethylammonioacetyl)-didodecyl-D-glutamate chloride (TMAG), N,N',N'',N'''-tetramethyl-N,N',N'',N'''-tetrapalmitylspermine (TMTPS), 2,3-dioleyloxy-N-[2(sperminecarboxamide)ethyl]-N,N-dimethyl-1-propanaminium trifluoroacetate (DOSPA), N-[1-(2,3-dioleyloxy)propyl]-N,N,N-trimethylammonium chloride (DOTMA), dioctadecyldimethylammonium chloride (DODAC), didodecylammonium bromide (DDAB), 1,2-dioleyloxy-3-trimethylammoniopropane (DOTAP), 3$\beta$-[N—(N',N'-dimethylaminoethane)carbamoyl] cholesterol (DC-Chol), 1,2-dimyristoyloxypropyl-3-dimethylhydroxyethylammonium (DMRIE), and O,O'-ditetradecanoyl-N-($\alpha$-trimethylammonioacetyl)diethanolamine chloride (DC-6-14).

The above carrier may have a specific 3-dimensional structure. Examples of such a structure include, but are not limited to, a straight-chain or branched linear structure, a film-like structure, and a spherical structure. Therefore, the carrier may have, without limitation, any 3-dimensional form such as a micelle, a liposome, an emulsion, a microsphere, or a nanosphere.

Binding of a retinoid and/or an active ingredient to a carrier or the inclusion thereof in a carrier may also be possible by binding the retinoid to a carrier or the inclusion thereof in a carrier by means of a chemical and/or physical method. Alternatively, binding of a retinoid and/or an active ingredient to a carrier or the inclusion thereof in a carrier may also be possible by mixing a retinoid and/or an active ingredient and a carrier-constituting component. The amount of retinoid in the composition of the present invention may be for example 0.01 to 1000 nmol/µL, and preferably 0.1 to 100 nmol/µL. Furthermore, the amount of active ingredient in the composition of the present invention may be for example 1 to 10000 ng/µL, and preferably 10 to 1000 ng/µL, or 1 to 1000000 µg/kg body weight, and preferably 10 to 100000 µg/kg body weight. The amounts of retinoid and active ingredient might, in some cases, be outside the above ranges depending on the activity of these components, the administration route of the composition, the administration frequency, the subject to which they are administered, etc., and these cases are also included in the scope of the present invention. Binding of a retinoid and/or an active ingredient to a carrier or the inclusion thereof in a carrier may be carried out prior to supporting an active ingredient on the carrier, may be carried out by simultaneously mixing a carrier-constituting component, a retinoid, and an active ingredient, or may be carried out by mixing a carrier having an active ingredient already supported thereon and a retinoid. Therefore, the present invention also relates to a method for producing a pharmaceutical composition for regenerating normal tissue from fibrotic tissue that includes a step of binding a retinoid to any existing drug-binding carrier or drug-encapsulating carrier, for example, a liposome preparation such as DaunoXome$^{(R)}$, Doxil, Caelyx$^{(R)}$, or Myocet$^{(R)}$.

The composition of the present invention may be in any form as long as a desired active ingredient can be transported to collagen-producing cells in fibrotic tissue as a target, and examples thereof include, but are not limited to, a polymer micelle, a liposome, an emulsion, a microsphere, and a nanosphere. In the present invention, from the viewpoint of high efficiency of delivery, wide choice of substances to be delivered, ease of preparation, etc., among the above a liposome form is preferable, and a cationic liposome that contains a cationic lipid is particularly preferable. When the composition is in the form of a liposome, the molar ratio of retinoid and liposome-constituting lipid is preferably 8:1 to 1:4, and more preferably 4:1 to 1:2, while taking into consideration the efficiency of binding of a retinoid to a carrier or the inclusion thereof in a carrier.

The composition of the present invention may contain an active ingredient in the interior, may have an active ingredient attached to the exterior, or may be mixed with an active ingredient. Therefore, the composition of the present invention may be in the form of a complex between a liposome and an active ingredient, that is a lipoplex; depending on the administration route, the manner in which the drug is released, etc., the composition may be coated with an appropriate material such as for example an enteric coating or a timed disintegration material, or may be incorporated into an appropriate drug release system.

When a retinoid is contained as a targeting agent, the retinoid is present in a form in which it functions as a targeting agent in the present composition. Here, functioning as a targeting agent means that the composition containing a retinoid reaches and/or is incorporated into a collagen-producing cell, which is the target cell, in fibrotic tissue at a higher speed and/or in a larger amount than that of a composition not containing the retinoid, and this can be easily confirmed by for example adding a labeled or label-containing composition to a culture of target cells and analyzing the site where the label is present after a predetermined time has elapsed. In terms of the structure, for example, if a retinoid is at least partially exposed to the exterior of the composition at the latest before it reaches the target cell, the above-mentioned requirements can be satisfied. Whether or not a retinoid is exposed to the exterior of the composition may be evaluated by contacting the composition with a substance that specifically binds to a retinoid, for example, a retinol-binding protein (RBP), etc., and examining binding to the composition.

Exposing a retinoid at least partially to the exterior of the composition at the latest before it reaches a target cell may be carried out by for example adjusting the compounding ratio of the retinoid and the carrier-constituting component. Furthermore, when a lipid structure such as a liposome is utilized as a carrier, for example, when forming a complex between the lipid structure and the retinoid, a method in which the lipid structure is first diluted in an aqueous solution, and this is then contacted, mixed, etc., with the retinoid may be used. In this case, the retinoid may be in a state in which it is dissolved in a solvent, for example, an organic solvent such as DMSO. The lipid structure referred to here means any 3-dimensional structure, for example, a structure having a linear, film-like, spherical, etc. shape and containing a lipid as a constituent component, and examples thereof include, but are not limited to, a liposome, a micelle, a lipid microsphere, a lipid nanosphere, and a lipid emulsion. The possibility of application to another drug carrier of the same targeting agent as that used for targeting of a liposome is described in for example Zhao and Lee, Adv Drug Deliv Rev. 2004; 56(8): 1193-204, Temming et al., Drug Resist Updat. 2005; 8(6): 381-402, etc.

In addition to a collagen-reducing substance, the composition of the present invention may contain a substance that reduces a fibrotic stimulus as an active ingredient, or may be used in combination with such a substance. Examples of the substance that reduces a fibrotic stimulus include, but are not limited to, an antioxidant, a blood circulation promoter, an anti-inflammatory drug, an antiviral drug, an antibiotic, an antiparasitic agent, a liver protection drug, a choleretic drug, and an apoptosis suppressor. These substances may be selected as appropriate according to the tissue that is targeted and the disease state.

The composition of the present invention may contain a label. Labeling enables the success/failure of delivery to target cells, the increase/decrease of target cells, etc. to be monitored, and is useful not only at the test and research level but also at the clinical level. The label may be selected from any label known to a person skilled in the art such as for example any radioisotope, magnetic material, substance that binds to a labeled substance (e.g. an antibody), fluorescent substance, fluorophore, chemiluminescent substance, or enzyme. Labeling may be affixed to at least one constituent component of the composition of the present invention; for example, when a retinoid is contained as a targeting agent, it may be affixed to one or more of an active ingredient, the retinoid, and a carrier-constituting component, or labeling may be contained in the composition as a component other than the above.

The term 'for collagen-producing cells in fibrotic tissue' or 'for delivery to collagen-producing cells in fibrotic tissue' in the present invention means that it is suitable to use collagen-producing cells in fibrotic tissue as target cells, and this includes for example being able to deliver a substance to said cells at a higher speed, a higher efficiency, and/or in a larger amount than for other cells, for example, normal cells. For example, the carrier for collagen-producing cells in fibrotic tissue or the carrier for delivery to collagen-producing cells in fibrotic tissue can deliver an active ingredient to collagen-producing cells in fibrotic tissue at a speed and/or efficiency of at least 1.1 times, at least 1.2 times, at least 1.3 times, at least 1.5 times, at least 2 times and, moreover, at least 3 times compared with other cells. Since the composition of the present invention contains a targeting agent for collagen-producing cells in fibrotic tissue, it can be made as a composition for collagen-producing cells in fibrotic tissue or for delivery to collagen-producing cells in fibrotic tissue.

The composition of the present invention may be used as a medicine (that is, a pharmaceutical composition) and may be administered via various types of routes including oral and parenteral routes; examples thereof include, but are not limited to, oral, enteral, intravenous, intramuscular, subcutaneous, local, intrahepatic, intrabiliary, intrapulmonary, tracheobronchial, intratracheal, intrabronchial, nasal, intrarectal, intraarterial, intraportal, intraventricular, intramedullary, intra-lymph node, intralymphatic, intracerebral, intrathecal, intracerebroventricular, transmucosal, percutaneous, intranasal, intraperitoneal, and intrauterine routes, and it may be formulated in a dosage form that is suitable for each administration route. Such a dosage form and formulation method may be selected as appropriate from any known forms and methods (see e.g. 'Hyojun Yakuzaigaku' (Standard Pharmaceutical Science), Ed. by Yoshiteru Watanabe et al., Nankodo, 2003).

Examples of dosage forms suitable for oral administration include, but are not limited to, powder, granule, tablet, capsule, liquid, suspension, emulsion, gel, and syrup, and examples of dosage forms suitable for parenteral administration include injections such as an injectable solution, an injectable suspension, an injectable emulsion, and an injection in a form that is prepared at the time of use. Formulations for parenteral administration may be in a configuration such as an aqueous or nonaqueous isotonic aseptic solution or suspension.

The composition of the present invention may be supplied in any configuration, but from the viewpoint of storage stability, it is provided in a configuration that can be prepared at the time of use, for example in a configuration that allows a doctor and/or a pharmacist, a nurse, another paramedic, etc. to prepare it at the place of treatment or in the vicinity thereof. In this case, the composition of the present invention is provided as one or more containers containing at least one essential constituent element therefor, and it is prepared prior to use, for example, within 24 hours prior to use, preferably within 3 hours prior to use, and more preferably immediately prior to use. When carrying out the preparation, a reagent, a solvent, preparation equipment, etc. that are normally available in a place of preparation may be used as appropriate.

The present invention therefore also relates to a preparation kit for the composition, the kit including one or more containers containing singly or in combination an active ingredient and/or an optional targeting agent or carrier-constituting substance, and also relates to a constituent element necessary for the composition provided in the form of such a kit. The kit of the present invention may contain, in addition to the above, instructions, an electronic recording medium such as a CD or DVD, etc. related to a preparative method and administration method for the composition of the present invention, etc. Furthermore, the kit of the present invention may include all of the constituent elements for completing the composition of the present invention, but need not always include all of the constituent elements. Therefore, the kit of the present invention need not include a reagent or a solvent that is normally available at a place of medical treatment, an experimental facility, etc. such as, for example, sterile water, physiological saline, or a glucose solution.

The present invention further relates to a method for regenerating normal tissue from fibrotic tissue, the method including a step of administering an effective amount of the composition or the collagen-reducing substance of the present invention to a subject that requires it. The effective amount referred to here is for example an amount that suppresses any increase in the amount of extracellular matrix such as collagen in fibrotic tissue, is preferably an amount that reduces the amount of extracellular matrix, and is more preferably an amount that causes regeneration of normal tissue in fibrotic tissue.

The amount of extracellular matrix may be quantitatively determined by various methods such as, for example, without limitation, image analysis of a specially stained image of extracellular matrix or measurement of an extracellular matrix marker. For example, collagen may be quantitatively determined by measuring the amount of a collagen marker such as hydroxyproline, or by subjecting tissue to collagen staining (e.g. Masson trichrome staining, Azan staining, sirius red staining, Elastica van Gieson staining, etc.) and carrying out an image analysis. The percentage reduction of extracellular matrix in fibrotic tissue may be for example at least 10%, at least 20%, at least 30%, at least 40%, at least 50%, at least 60%, at least 70% and, moreover, at least 75% compared with a case in which the composition of the present invention has not been administered. Here, the case in which the composition of the present invention has not been administered includes not only a case in which administration itself has not been carried out but also a case in which a vehicle alone has been administered, a case in which a composition corresponding to the composition of the present invention except that it does not contain the active ingredient has been administered and, when the composition of the present invention contains a targeting agent, a case in which a composition corresponding to the composition of the present invention except that it does not contain the targeting agent has been administered (so-called negative controls). Furthermore, regeneration of normal tissue may be evaluated by histological observation or by administration of labeled stem cells to fibrotic tissue and carrying out a tracking survey thereof.

The effective amount is preferably an amount that does not cause an adverse effect that exceeds the benefit from administration. Such an amount may be determined as appropriate by an in vitro test using cultured cells or by a test in a model animal such as a mouse, a rat, a dog, or a pig, and such test methods are well known to a person skilled in the art. Moreover, the dose of the drug used in the method of the present invention is known to a person skilled in the art, or may be determined as appropriate by the above-mentioned test, etc. As a model animal for fibrosis, various models such as a hepatic cirrhosis model obtained by carbon tetrachloride ($CCl_4$), porcine serum, dimethylnitrosamine (DMN), a methionine-choline deficient diet (MCDD), concanavalin A (Con A), bile duct ligation, etc., a pulmonary fibrosis model obtained by bleomycin (BLM), etc., a pancreatic fibrosis model obtained by dibutyltin dichloride, etc., and a myelofibrosis model such as a thrombopoietin (TPO) transgenic mouse (Leukemia Research 29: 761-769, 2005) may be used.

In the method of the present invention, the specific dose of the composition or collagen-reducing substance administered may be determined while taking into consideration various conditions with respect to the subject that requires the treatment, such as for example the severity of the symptoms, the general health condition of the subject, the age, weight, and gender of the subject, the diet, the timing and frequency of administration, a medicine used in combination, reaction to the treatment, compliance with the treatment, etc.

As the administration route, there are various routes including both oral and parenteral administration, and examples thereof include oral, enteral, intravenous, intramuscular, subcutaneous, local, intrahepatic, intrabiliary, intrapulmonary, tracheobronchial, intratracheal, intrabronchial, nasal, intrarectal, intraarterial, intraportal, intraventricular, intramedullary, intra-lymph node, intralymphatic, intracerebral, intrathecal, intracerebroventricular, transmucosal, percutaneous, intranasal, intraperitoneal, and intrauterine routes.

The frequency of administration depends on the properties of the composition used and the above-mentioned condition of the subject, and may be a plurality of times per day (that is, 2, 3, 4, 5, or more times per day), once a day, every few days (that is, every 2, 3, 4, 5, 6, or 7 days, etc.), a few times per week (e.g. 2, 3, 4 times, etc. per week), every week, or every few weeks (that is, every 2, 3, 4 weeks, etc.).

In the method of the present invention, the term 'subject' means any living individual, preferably an animal, more preferably a mammal, and yet more preferably a human individual. In the present invention, the subject may be healthy or affected by some disorder, but it typically means a subject having fibrotic tissue or tissue having a risk of becoming fibrotic. Examples of such a subject include, but are not limited to, a subject affected by the above organ fibrosis or having a risk of being affected and a subject for which tissue is receiving a fibrotic stimulus or has a risk of receiving it.

The present invention further relates to a method for regenerating normal tissue from fibrotic tissue, the method including a step of reducing collagen in the fibrotic tissue and/or a step of forming a space for cell growth and differentiation in the fibrotic tissue.

In the present method, reduction of collagen in fibrotic tissue and formation of a space for cell growth and differentiation may be carried out by administering the composition of the present invention or the above-mentioned collagen-reducing substance to fibrotic tissue.

EXAMPLES

The present invention is explained in further detail by means of the Examples below, but they are only illustrations and do not in any way limit the present invention. In the Examples below, data are expressed as average values (±standard deviation). Multiple comparisons between a control group and another group were carried out by means of Dunnett's test.

Example 1

Preparation of VA-Lip siRNA (1) Preparation of siRNA

As a sense chain and an antisense chain of siRNA (Hokkaido System Science Co., Ltd., Sapporo, Japan) targeted to the base sequence of gp46 (GenBank Accession No. M69246), which is the rat homologue of human HSP47, a molecular chaperone common to collagens (types I to IV), those below were used.

```
A:
GUUCCACCAUAAGAUGGUAGACAACAG
(sense chain siRNA starting from
the 757th base on the gp46 base
sequence, SEQ ID NO: 1)

B:
GUUGUCUACCAUCUUAUGGUGGAACAU
(antisense chain siRNA, SEQ ID NO: 2)
```

As siRNA random (also called siRNAscramble), those below were used.

```
C:
CGAUUCGCUAGACCGGCUUCAUUGCAG
(sense chain siRNA, SEQ ID NO: 3)

D:
GCAAUGAAGCCGGUCUAGCGAAUCGAU
(antisense chain siRNA, SEQ ID NO: 4)
```

In some experiments, sense chains having 6'-carboxyfluorescein (6-FAM) or fluorescein isothiocyanate (FITC) conjugated to the 5' terminal were used. It was confirmed by a BLAST search that these sequences did not have homology with other known rat mRNA.

(2) Preparation of VA-Lip siRNA

As a cationic lipid, a cationic liposome (LipoTrust) containing O,O'-ditetradecanoyl-N-(α-trimethylammonioacetyl)diethanolamine chloride (DC-6-14), cholesterol, and dioleylphosphatidylethanolamine (DOPE) at a molar ratio of 4:3:3 was purchased from Hokkaido System Science Co., Ltd. (Sapporo, Japan). Before use, the liposome was prepared at a concentration of 1 mM (DC-6-14) by adding doubly distilled water (DDW) to a lyophilized lipid mixture while stirring. In order to prepare a VA coupled liposome, 200 nmol vitamin A (retinol, Sigma, USA) dissolved in DMSO was mixed with a liposome suspension (100 nmol as DC-6-14) in a 1.5 mL tube while stirring at 25° C. In order to prepare a VA coupled liposome supporting siRNAgp46 (VA-lip-siRNAgp46), an siRNAgp46 solution (580 pmol/mL in DDW) was added to the retinol coupled liposome solution while stirring at room temperature. The molar ratio of siRNA and DC-6-14 was 1:11. In order to obtain a desired dose in vitro, the VA-lip siRNA was reconstituted using phosphate buffered saline (PBS).

Example 2

Regenerative Therapy Experiment Using Hepatic Fibrosis Model Rat (1) Preparation of Hepatic Fibrosis Model Rat A hepatic fibrosis model rat was prepared by subjecting a male SD rat (body weight 150 to 200 g) (Slc Japan, Shizuoka, Japan) to common bile duct ligation, and an individual on the 28th day after ligation was subjected to the present experiment. The present model rat was in a state in which cholestasis was caused by the common bile duct ligation and the liver tissue was continually exposed to a fibrotic stimulus.

(2) Preparation of GFP-Labeled Rat Hepatic Stem Cells

GFP-labeled rat hepatic stem cells were harvested from the liver of a 4 week old GFP transgenic rat (Slc Japan). First, an EGTA solution and a collagenase solution were perfused through the GFP transgenic rat, the liver was then harvested, and the harvested liver was finely cut and then filtered using a cell strainer (pore diameter 100 μm). Hank's balanced salt solution (HBSS)+0.25% bovine serum albumin (BSA) solution were added to the cell suspension obtained, and the mixture was subjected to centrifugation at 4° C. and 500 rpm for 2 minutes. The supernatant was harvested and subjected to centrifugation at 4° C. and 1300 rpm for 5 minutes. After the supernatant was removed, MACS® (Magnetic Activating Cell Sorting) buffer (Miltenyi Biotec, Auburn, Calif., USA) was added to the precipitate and mixed. After the number of cells was counted, MACS® was carried out using an FITC conjugated mouse anti-CD45 antibody (BD Pharmingen), a rabbit polyclonal anti-CD133 antibody (Abcam), and a mouse monoclonal anti-EpCAM antibody (Santa Cruz), and CD133-positive, EpCAM-positive, and CD45 negative cells were harvested and used as rat hepatic stem cells in the present experiment.

(3) Treatment of Hepatic Fibrosis Model Rat

The GFP-labeled hepatic stem cells prepared in (2) were locally transplanted in hepatic fibrosis model rats prepared in (1) at a concentration of $2 \times 10^6$ counts in 200 μL of DME/F12 medium.

From 24 hours after transplantation of the hepatic stem cells, vitamin A coupled liposome-encapsulated siRNAgp46 (VA-lip siRNAgp46) or VA-lip siRNAscramble as a mock was administered via the tail vein every other day a total of 12 times. The concentration of siRNA administered was 0.75 mg/kg rat body weight. The molar ratio of vitamin A, liposome (LipoTrust, Hokkaido System Science Co., Ltd., Sapporo, Japan), and siRNA was 11.5:11.5:1.

(4) Tissue Staining 24 hours after the 12th administration of VA-lip siRNAgp46 in (3) (that is, on the 52nd day after the common bile duct ligation), the liver of the common bile duct ligation rat to which the GFP expressing hepatic stem cells had been transplanted was harvested. After the harvested liver was embedded using OCT compound, frozen sections were prepared. The liver sections were fixed using 4% paraformaldehyde. Some of the sections were subjected to Azan-staining by a standard method. Some of the sections were subjected to blocking with PBS containing 5% goat serum, washed with PBS, and then reacted at 4° C. overnight using a mouse monoclonal anti-α smooth muscle actin (α-SMA) antibody (Sigma), a mouse monoclonal anti-glial fibrillary acidic protein (GFAP) antibody (Sigma), a rabbit polyclonal anti-albumin antibody (MP Biomedicals), a mouse monoclonal anti-CK19 antibody (Novocastra), and a mouse monoclonal anti-vascular endothelium cadherin (ve-CAD, Vascular Endothelial Cadherin) antibody (Santa Cruz). After washing with PBS, they were reacted with an Alexa555-labeled goat anti-mouse IgG antibody and an Alexa555-labeled goat anti-rabbit IgG antibody (both from Invitrogen) at room temperature for 60 minutes. After washing with PBS, they were embedded using ProLong(R) Gold with DAPI (Invitrogen) and examined by means of a fluorescence microscope. Instead of the reaction with goat anti-rabbit antibody, some portion of the sections were reacted with an α-SMA antibody (Dako) and then subjected to coloration by means of diaminobenzidine (DAB) and further to nuclear staining by means of hematoxylin.

Results

FIG. 1 shows the appearance of livers harvested from the test rats and Azan-stained images of representative sections thereof. In the group to which VA-lip siRNAscramble had been administered, the liver contracted, the surface was irregular, accumulation of extracellular matrix that had been stained was observed widely in the tissue in the Azan-stained image, and the hepatic lobule structure was disturbed. On the other hand, in the group to which VA-lip siRNAgp46 had been administered, there was no apparent contraction, the surface was smooth, there was hardly any accumulation of extracellular matrix in the tissue, and there was a clear reduction in the size of the fibrotic region compared with the VA-lip siRNAscramble-treated group. Furthermore, it was clearly observed that a normal hepatic lobule structure, in which the sinusoids run radially from the central vein, had recovered.

Figure 2:
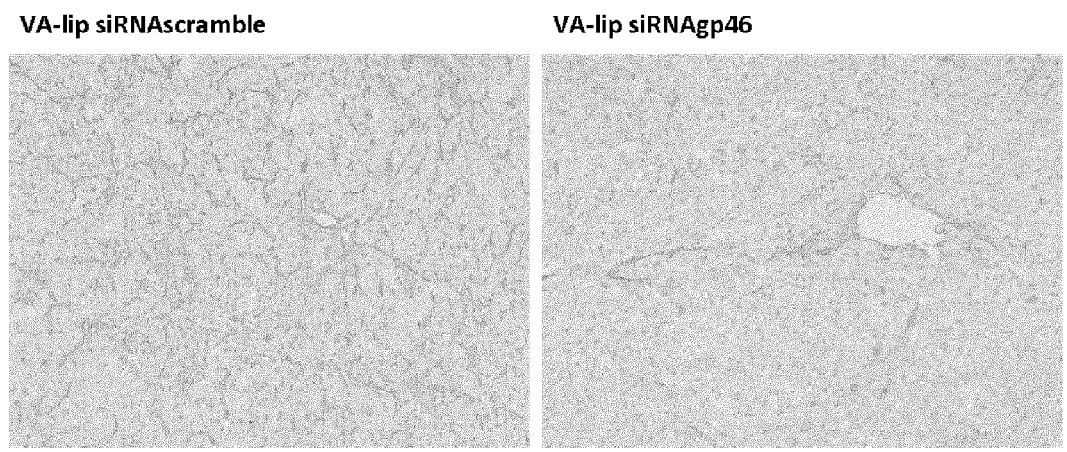
FIG. 2 is a photographic diagram showing the localization of α-SMA in representative sections of liver harvested from test rats.

FIG. 2 shows α-SMA antibody DAB-stained images. The nucleus is hematoxylin-stained, and dark portions are α-SMA-positive regions. α-SMA is known as a marker for activated stellate cells, and it is thought that in the α-SMA-positive regions activated stellate cells are present. In the VA-lip siRNAgp46-treated group there was a marked reduction in the activated stellate cells compared with VA-lip siRNAscramble.

FIG. 3 shows DAPI and GFP fluorescence images of GFP-labeled hepatic stem cell transplantation sites. In the VA-lip siRNAgp46-treated group, GFP coloration was observed in about 80% of the region, whereas in the VA-lip siRNAscramble-treated group there was hardly any coloration.

FIG. 4 shows bright field and GFP fluorescence images of GFP-labeled hepatic stem cell transplantation sites. In the VA-lip siRNAscramble-treated group, the shape of cells became blurred due to accumulation of extracellular matrix, particularly in areas around blood vessels, and the sinusoids ran in a random fashion, whereas in the VA-lip siRNAgp46-treated group the cell shape was clear and a sinusoid structure in which they ran radially from the central vein was observed. Furthermore, in the VA-lip siRNAscramble-treated group there was no GFP coloration, whereas in the VA-lip siRNAgp46-treated group GFP coloration was observed throughout the tissue.

Figure 5A:
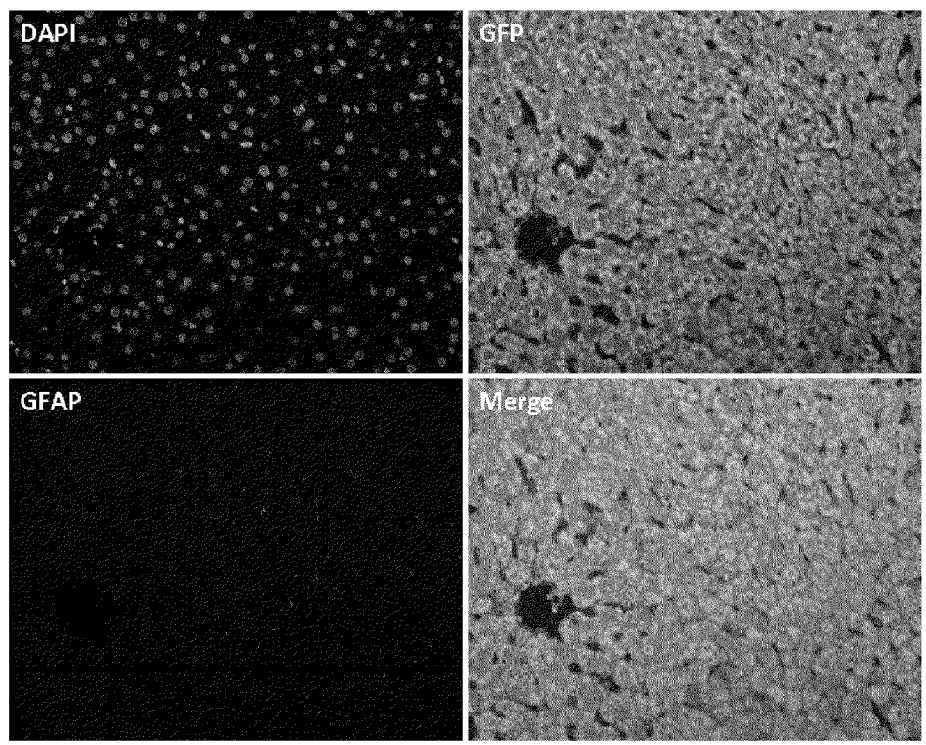
FIG. 5 A is a photographic diagram comparing DAPI and GFP fluorescence images and an image fluorescently stained by a GFAP antibody in a VA-lip siRNAgp46-treated group (200× magnification).
Figure 5B:
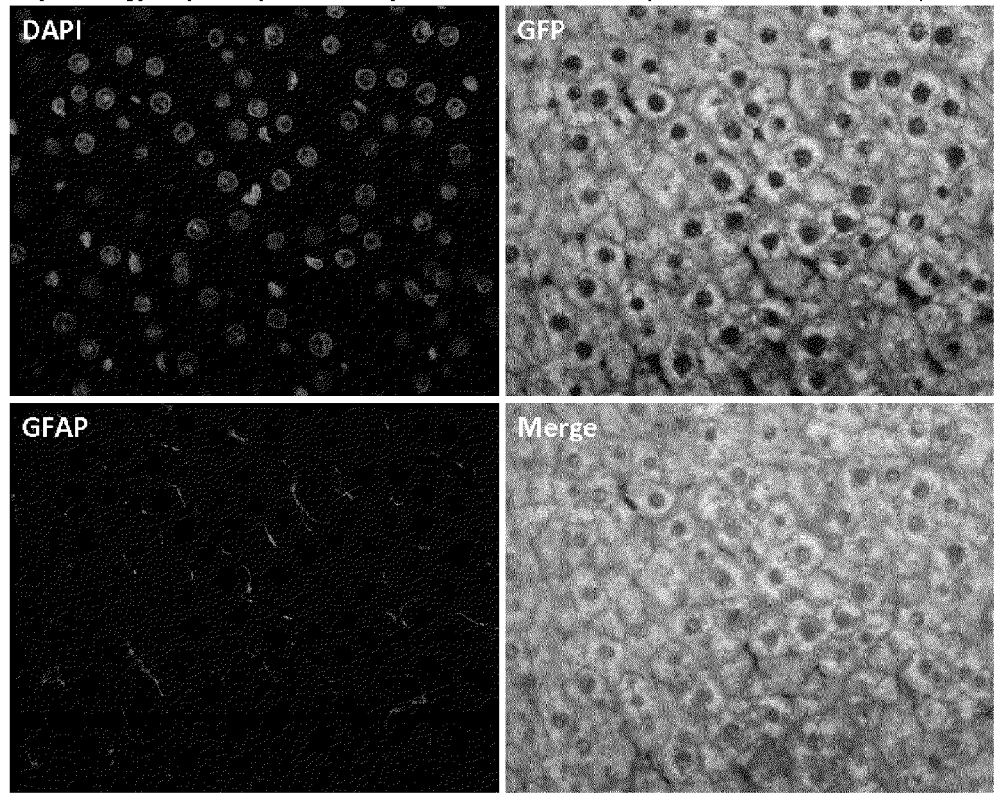

FIG. 5 is a comparison between DAPI and GFP fluorescence images and an image fluorescently stained by a GFAP antibody in the VA-lip siRNAgp46-treated group (FIG. 5A is 200× magnification and FIG. 5B is 400× magnification). GFAP is a protein known as a marker for hepatic stellate cells in a resting state. Cells expressing GFAP were not expressing GFP.

Figure 6:
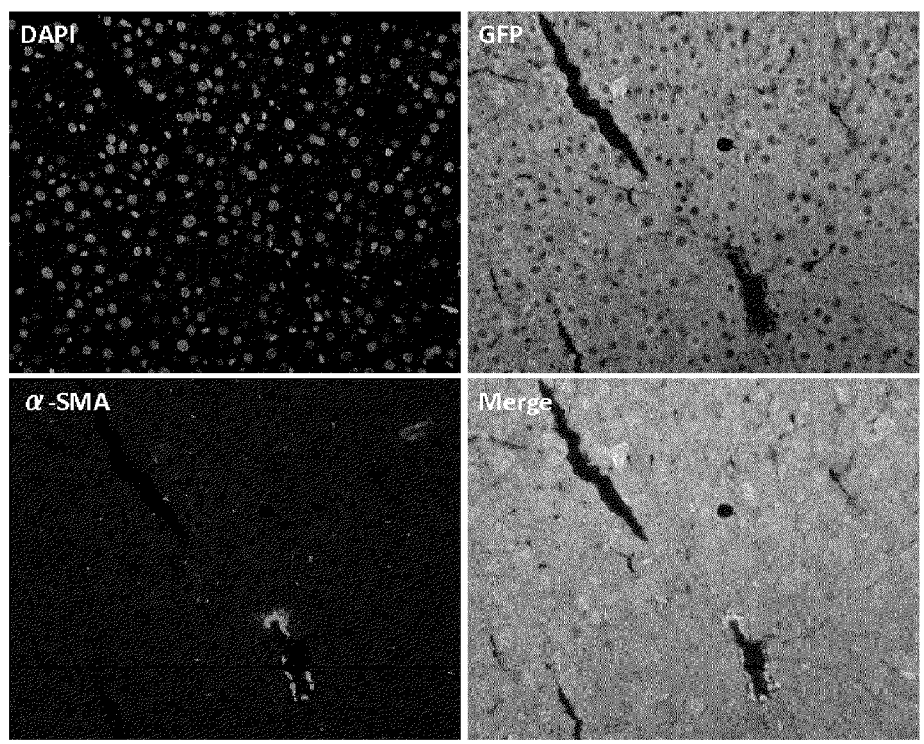
FIG. 6 is a 200× magnification photographic diagram comparing DAPI and GFP fluorescence images and an image fluorescently stained by an α-SMA antibody in a VA-lip siRNAgp46-treated group.

FIG. 6 is a comparison between DAPI and GFP fluorescence images and an image fluorescently stained by α-SMA antibody in the VA-lip siRNAgp46-treated group at 200× magnification. Cells expressing α-SMA were not expressing GFP. The results of FIGS. 5 and 6 suggest that hepatic stellate cells are not derived from hepatic stem cells.

Figure 7:
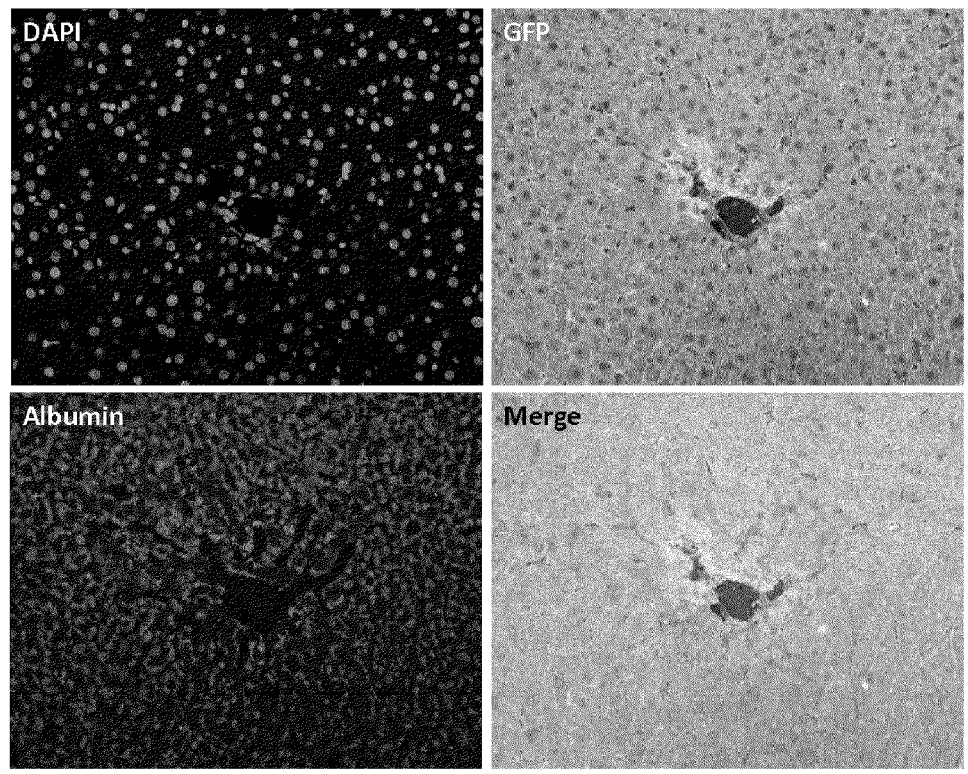
FIG. 7 is a 200× magnification photographic diagram comparing DAPI and GFP fluorescence images and an image fluorescently stained by an albumin antibody in a VA-lip siRNAgp46-treated group.

FIG. 7 is a comparison between DAPI and GFP fluorescence images and an image fluorescently stained by albumin antibody in the VA-lip siRNAgp46-treated group at 200× magnification. Albumin is a marker for hepatocytes, and many of the cells expressing GFP were expressing albumin.

Figure 8:
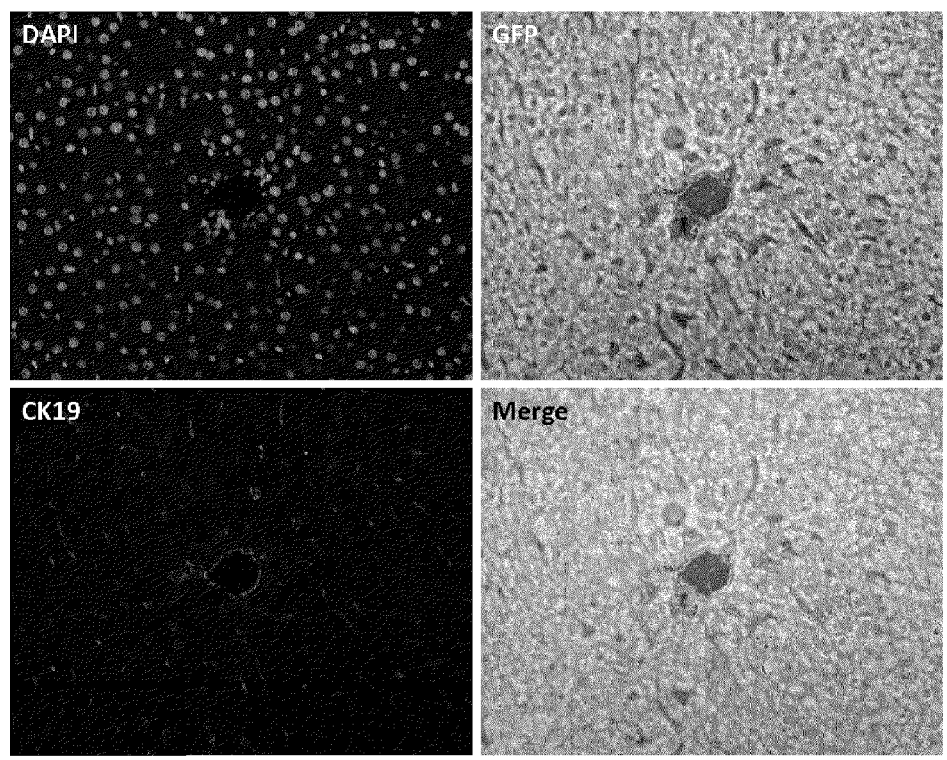
FIG. 8 is a 200× magnification photographic diagram comparing DAPI and GFP fluorescence images and an image fluorescently stained by a CK19 antibody in a VA-lip siRNAgp46-treated group.

FIG. 8 is a comparison between DAPI and GFP fluorescence images and an image fluorescently stained by CK19 antibody in the VA-lip siRNAgp46-treated group at 200× magnification. CK19 is a marker for bile duct epithelial cells, and CK19-positive cells forming the bile duct were expressing GFP.

Figure 9A:
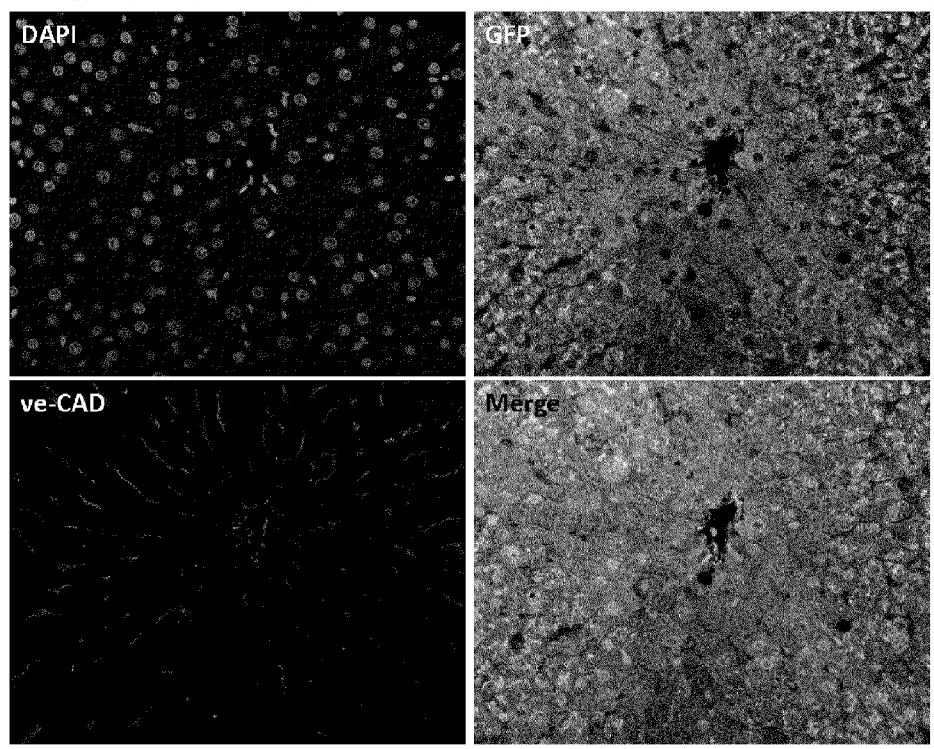
FIG. 9 A is a photographic diagram comparing DAPI and GFP fluorescence images and an image fluorescently stained by a ve-CAD antibody in a VA-lip siRNAgp46-treated group (200× magnification).
Figure 9B:
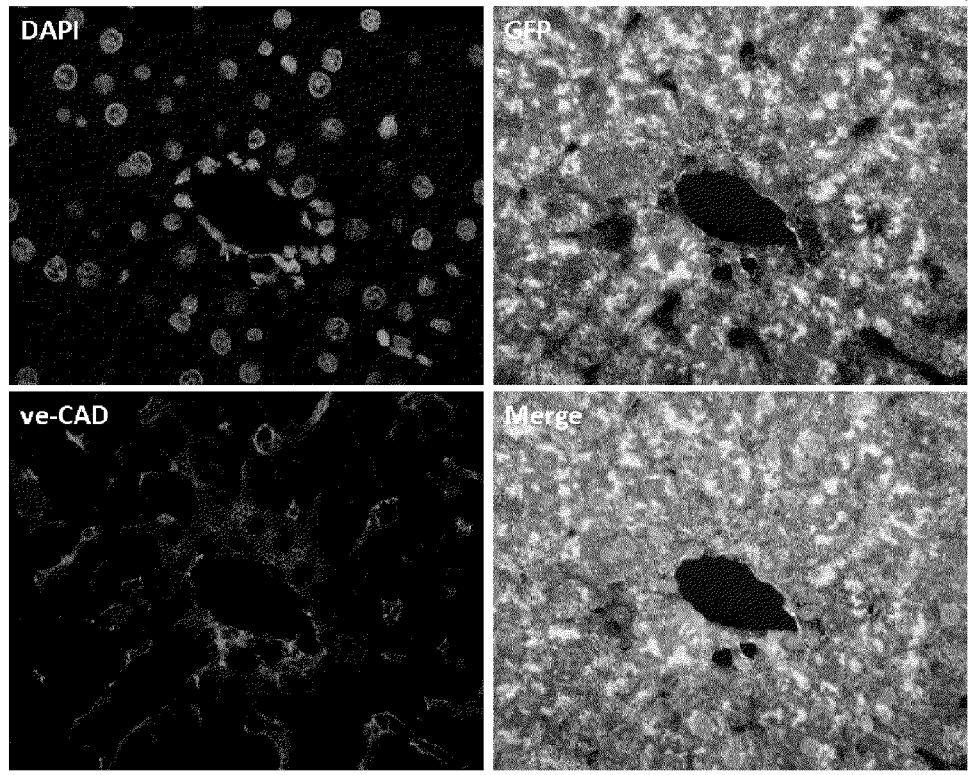

FIG. 9 is a comparison between DAPI and GFP fluorescence images and an image fluorescently stained by ve-CAD antibody in the VA-lip siRNAgp46-treated group (FIG. 9A is 200× magnification and FIG. 9B is 400× magnification). ve-CAD is known as a marker for blood vessel epithelial cells, and in some of the cells expressing GFP cells, cells expressing ve-CAD were observed.

Figure 10:
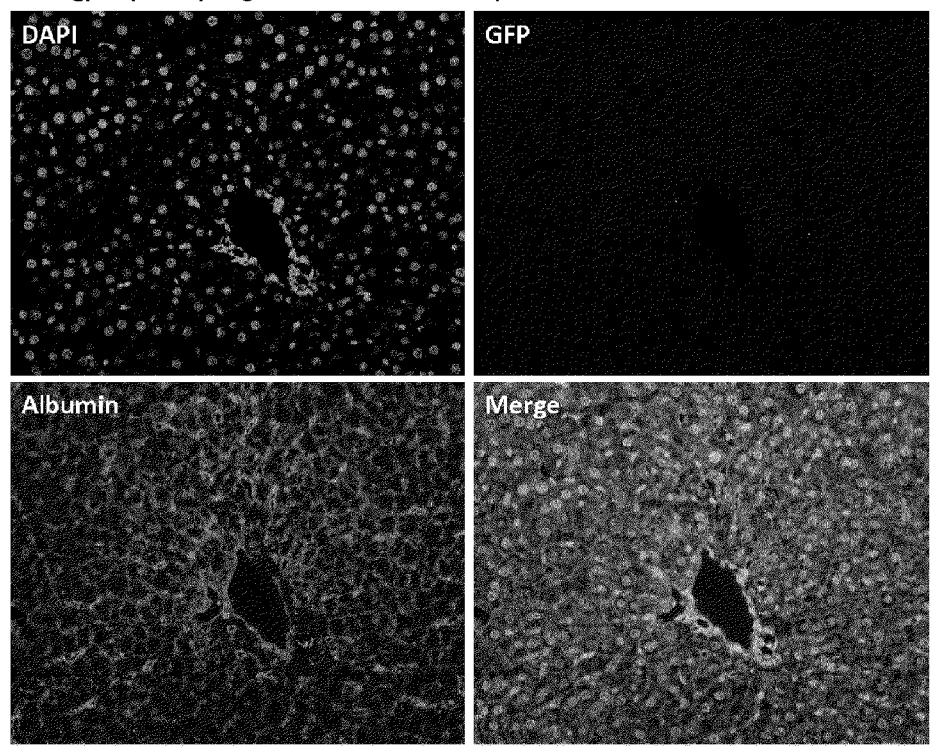
FIG. 10 is a 200× magnification photographic diagram comparing DAPI and GFP fluorescence images and an image fluorescently stained by an albumin antibody in a site of a VA-lip siRNAgp46-treated group where hepatic stem cells were not transplanted.

FIG. 10 is a comparison between DAPI and GFP fluorescence images and an image fluorescently stained by albumin antibody in a site of the VA-lip siRNAgp46-treated group where cells had not been transplanted at 200× magnification. In the site where cells had not been transplanted, there were no GFP-expressing cells.

Discussion

Since cells that expressed GFP were cells derived from the transplanted hepatic stem cells, due to administration of VA-lip siRNAgp46, in the cell-transplantation site the fibrotic region reduced in size and hepatic stem cells differentiated to hepatocytes, bile duct epithelial cells, and blood vessel epithelial cells, thus showing that normal liver tissue was regenerated. That is, it has become clear that treatment involving administration of VA-lip siRNAgp46 not only cures hepatic fibrosis but also induces liver regeneration. Furthermore, the result that in the VA-lip siRNAscramble-treated group no hepatic stem cells could be detected (FIG. 3) suggests that the reduction in size of the fibrotic region due to VA-lip siRNAgp46 is deeply involved in the growth and differentiation of hepatic stem cells.

Example 3

Stellate Cell-Specific Delivery by Means of VA (1) Isolation of Rat Pancreatic Stellate Cells (PSC)

Rat pancreatic stellate cells (PSC) were isolated using a density gradient centrifugation method in accordance with a previous report (Apte et al. Gut 1998; 43: 128-133). Purity was assayed by microscopic examination, autofluorescence of endogenous VA, and an immunocytochemical method using a monoclonal antibody (1:25, Dako) for desmin, which is a muscle actin crosslinking protein. The viability of cells was assayed by trypan blue exclusion. Both the cell purity and the viability exceeded 95%. The cells were cultured in Iscove's modified Dulbecco's medium (Iscove's modified Dulbecco's medium: IMDM) supplemented with 10% fetal bovine serum (FBS) at 37° C. with 95% air/5% $CO_2$ under a humidified environment.

(2) Intracellular Distribution Analysis of VA-Lip siRNAgp46-FAM

Rat pPSCs (primary pancreatic stellate cells, primary PSC) were sown so that there were 1×10⁴ cells per chamber in a Lab-Tek chamber cover glass. VA-lip siRNAgp46-FAM or Lip siRNAgp46-FAM was added to the cells so that the final siRNA concentration was 50 nM. The cells were cultured in 10% FBS-containing DMEM for 30 minutes, and the medium was exchanged with fresh medium. 30 minutes after and 2 hours after the treatment the cells were washed with PBS three times, and were fixed by treating with 4% paraformaldehyde at 25° C. for 15 minutes. After fixation, the cells were washed with PBS three times and exposed to ProLong$^{(R)}$ Gold with DAPI (Invitrogen) for 1 minute to thus stain the nucleus. Intracellular localization of FAM-labeled siRNAgp46 was assayed using a fluorescence microscope (Keyence, BZ-8000).

(3) FACS Analysis of VA-Lip siRNAgp46-FAM

Rat pPSCs (1×10⁴ cells) were treated with VA-lip siRNAgp46-FAM (50 nM siRNA) in the presence of 10% FBS and cultured for 30 minutes. For a blocking assay, before VA-lip siRNAgp46-FAM was added, 1×10⁴ cells were treated with a mouse anti-RBP antibody (10 μg/mL, BD Pharmingen), or mouse $IgG_1$ (10 μg/mL, Dako) as a negative control, for 30 minutes. The mean fluorescence intensity (MFI) of VA-lip siRNAgp46-FAM-treated cells was assayed using a FACScalibur with CellQuest software (Becton Dickinson).

(4) Western Blotting

In order to evaluate the knockdown effect of siRNAgp46, a Western blotting experiment was carried out. Specifically, protein extracts of PSCs respectively treated with VA-lip siRNAgp46 (1 nM, 5 nM, 50 nM), VA-lip-siRNA random (50 nM), and Lip-siRNAgp46 (50 nM) for 30 minutes were separated by means of 4/20 SDS-polyacrylamide gel, transferred to nitrocellulose film, probed with an antibody (Stressgen) for HSP47 (gp46) or an antibody (Cell Signaling) for β-actin, and labeled with a peroxidase-bound antibody (Oncogene Research Products, Boston, Mass.) as a secondary antibody. Finally, the cells were visualized by means of an ECL Western blotting detection system (Amersham Life Science, Arlington Heights, Ill.).

Furthermore, in order to confirm the duration of suppression of expression of gp46, PSCs were treated with VA-lip siRNAgp46 (50 nM) for 30 minutes and then cultured for 24 hours, 48 hours, 72 hours, and 96 hours, and following this protein was extracted and subjected to a Western blotting experiment in the same way as described above, together with one 30 minutes after treatment with VA-lip-siRNA random (50 nM).

(5) Quantitative Determination of Production of Collagen

Rat pPSCs were sown on a 6-well tissue culture plate at a density of 5×10⁴ cells/well in 10% FBS-containing DMEM. After culturing for 24 hours, the rat pPSCs were treated with VA-lip siRNAgp46 (50 nM siRNA) and VA-lip siRNA random (50 nM siRNA). The cells were cultured in 10% FBS-containing DMEM for 30 minutes, and the medium was then exchanged with fresh medium. 72 hours after the treatment, the cells were washed with PBS three times, and collagen deposited in the well was stained using sirius red (Biocolor, Belfast, UK) in accordance with a previous report (Williams et al. Gut 2001; 49: 577-583). Unbound dye was removed by washing, and bound complex was dissolved in 0.5% sodium hydroxide. Quantitative analysis of collagen was carried out by absorption intensity analysis at 540 nm, and the result was expressed as a percentage relative to an untreated control.

Results

Figure 11:
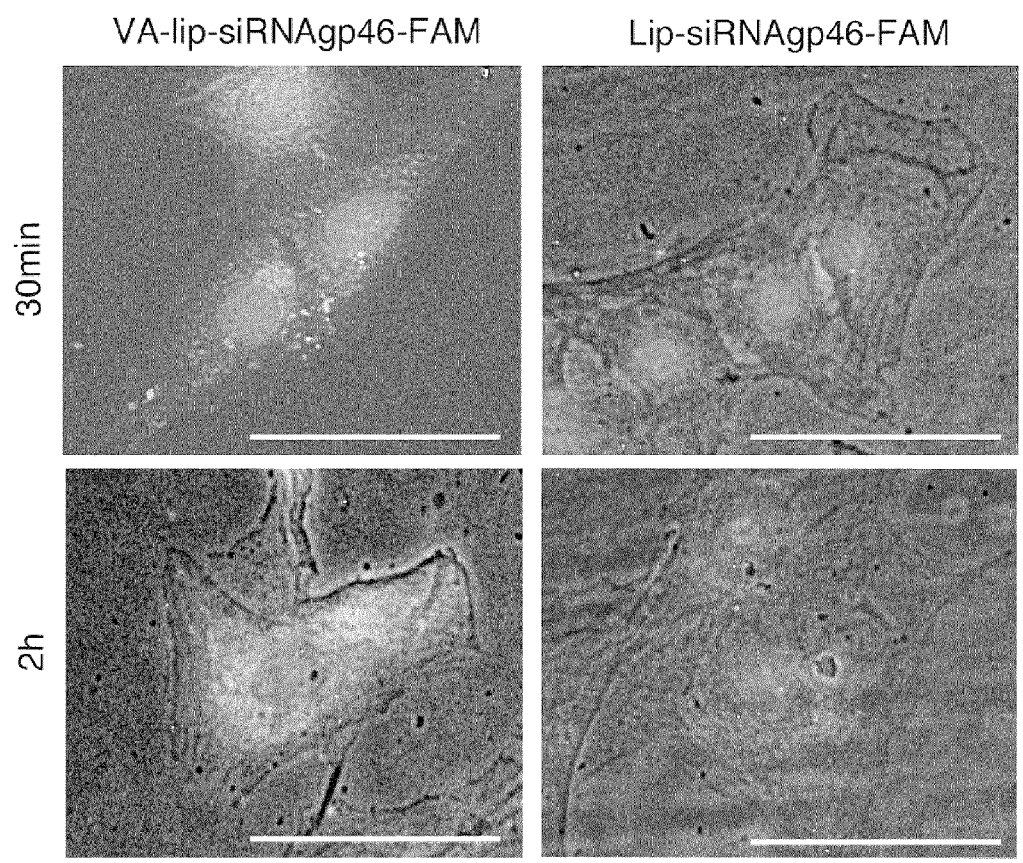
FIG. 11 is a fluorescence image showing the intracellular distribution of FAM-labeled siRNA in rat pancreatic stellate cells.

FIG. 11 shows fluorescence images of the intracellular distribution of FAM-labeled siRNA. The two images on the left are fluorescence images of PSCs treated with VA-lip siRNAgp46-FAM, and the two images on the right are fluorescence images of PSCs treated with Lip siRNAgp46-FAM. The upper two images are images 30 minutes after the treatment, and the lower two images are images 2 hours after the treatment. 30 minutes after the treatment With VA-lip siR- NAgp46-FAM, faint fluorescence due to FAM in a granular pattern was observed within the cytoplasm, and 2 hours after the treatment, a darker granular pattern was observed in a region around the nucleus. In comparison therewith, in the Lip siRNAgp46-FAM-treated group, no fluorescence was observed 30 minutes after the treatment, and fluorescence around the nucleus 2 hours after the treatment was faint.

Figure 12:
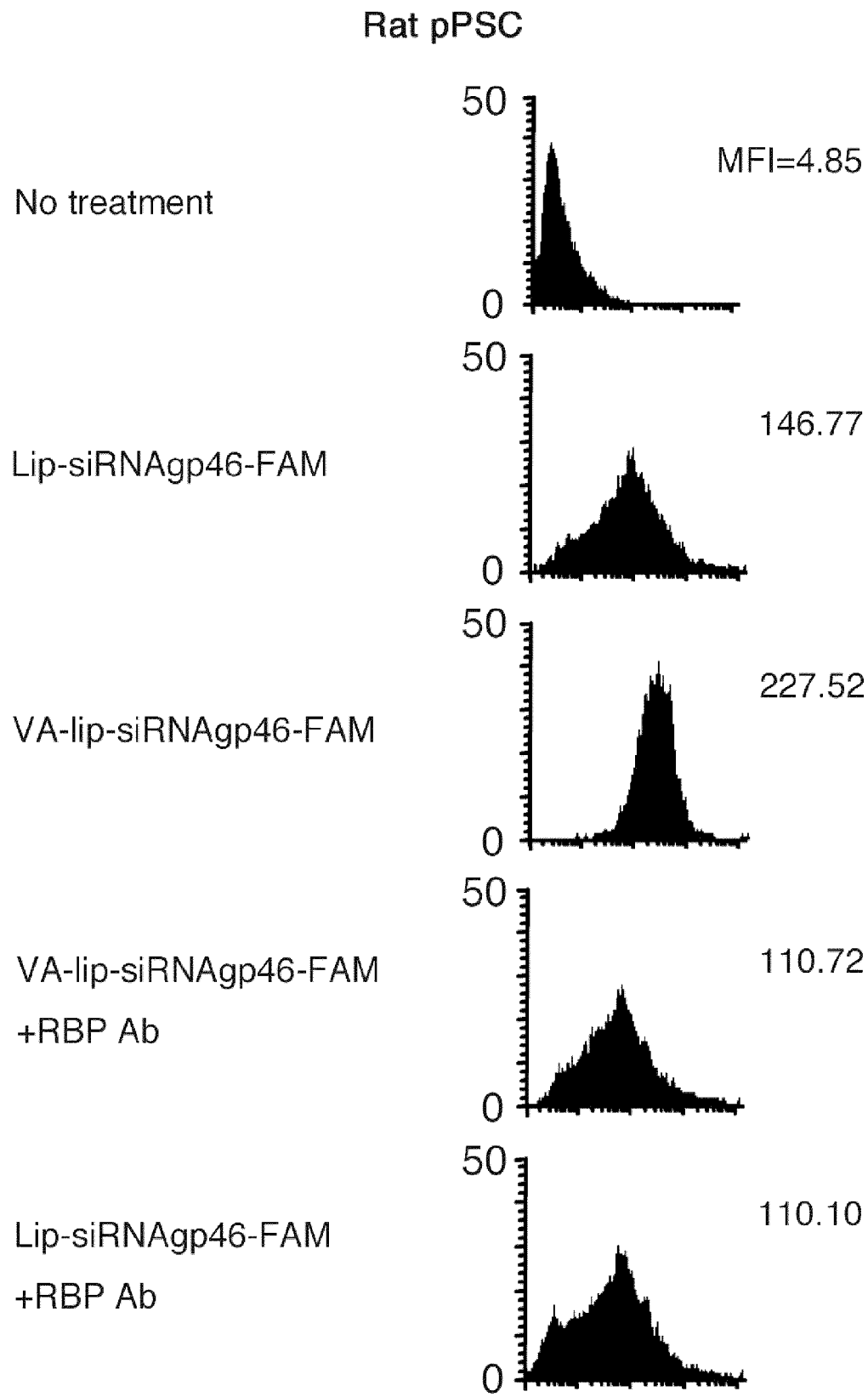
FIG. 12 is a graph showing the result of a FACS analysis with respect to siRNA incorporated into rat pancreatic stellate cells. Respectively shown in sequence from the top are the results of an untreated group, a Lip siRNAgp46-FAM-treated group, a VA-lip siRNAgp46-FAM-treated group, a VA-lip siRNAgp46-FAM+RBP antibody-treated group, and a Lip siRNAgp46-FAM+RBP antibody-treated group.

FIG. 12 shows graphs of the results of the FACS analysis. The results of the non-treated group, the Lip siRNAgp46-FAM-treated group, the VA-lip siRNAgp46-FAM-treated group, the VA-lip siRNAgp46-FAM+RBP antibody-treated group, and the Lip siRNAgp46-FAM+RBP antibody-treated group are shown in sequence from the top. In the results of the FACS analysis, compared with the VA-lip siRNAgp46-FAM-treated group, in the VA-lip siRNAgp46-FAM+RBP antibody-treated group, the fluorescence strength was suppressed to the same level as that of the Lip siRNAgp46-FAM-treated group, suggesting that the incorporation of VA-lip siRNAgp46 into PSCs is mediated by an RBP receptor.

FIG. 13 A shows the results of Western blotting, which show the difference in suppression effect according to concentration. In the cells treated with VA-lip siRNAgp46, suppression of the expression of gp46 was observed to be dependent on the concentration of VA-lip siRNAgp46, the expression being almost completely suppressed at 50 nM, whereas suppression of expression was not observed with VA-lip siRNA random or Lip siRNAgp46.

FIG. 13 B shows the result of Western blotting for ascertaining the duration of the suppression effect. When treated with VA-lip siRNAgp46, in cells cultured for 72 hours after the treatment, marked suppression of gp46 was observed. Therefore, it was confirmed that the effect of suppressing the expression of gp46 continued for at least 72 hours after the treatment.

Figure 14:
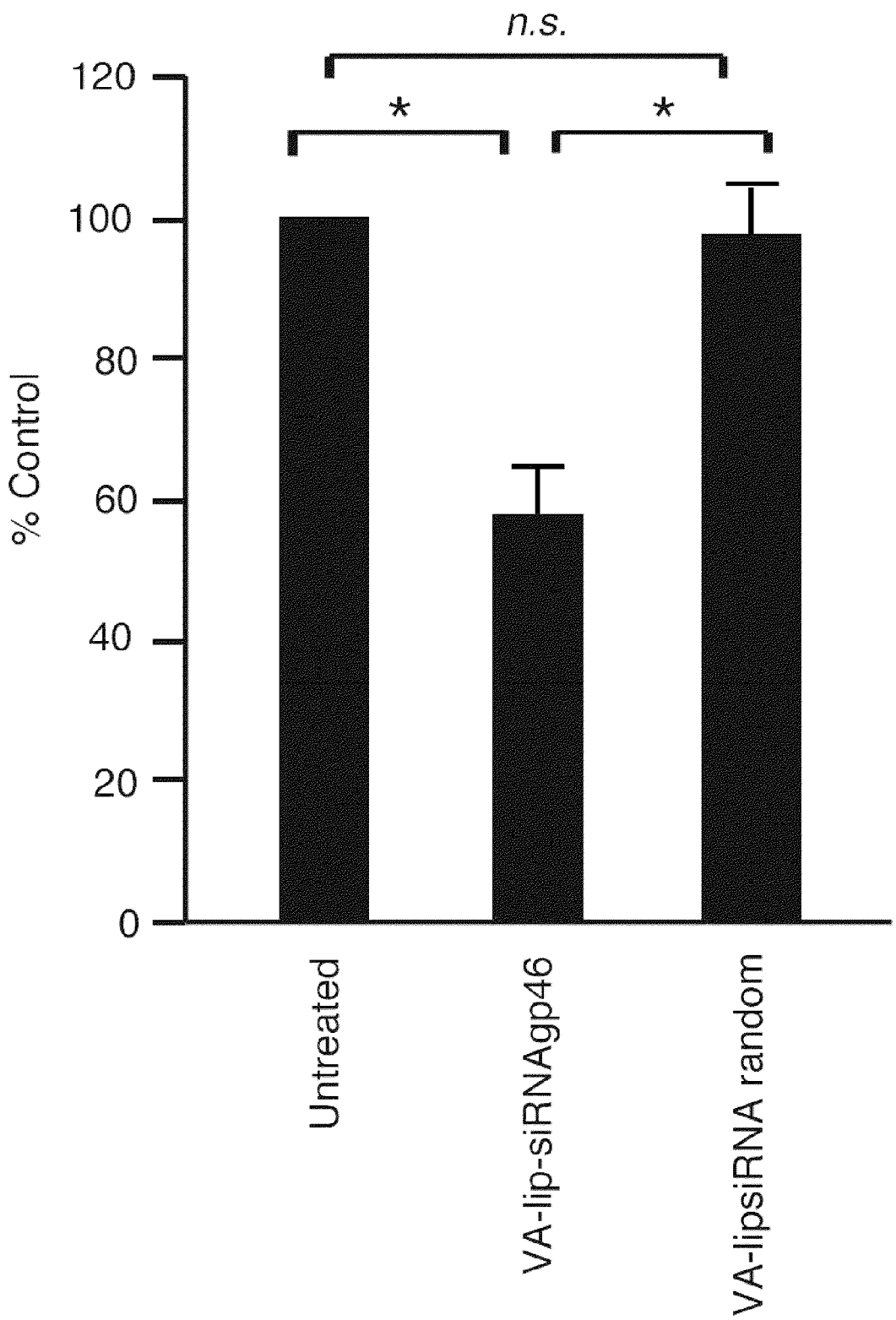
FIG. 14 is a graph showing the quantitative amounts of collagen produced after 72 hours by untreated cells and cells treated with each of VA-lip siRNAgp46 and VA-lip siRNA random.

FIG. 14 is a graph showing quantitative determination of the amount of collagen produced after 72 hours in non-treated cells and cells treated with VA-lip siRNAgp46 and VA-lip siRNA random respectively. Compared with the untreated cells and the cells treated with VA-lip siRNA random, when treated with VA-lip siRNAgp46, marked suppression of the production of collagen was confirmed.

Discussion

From the results above it can be seen that, in vitro, VA-lip siRNAgp46 is incorporated specifically into PSCs by RBP receptor-mediated incorporation to thus suppress the expression of gp46, and as a result, the production of collagen is markedly suppressed. This suggests that in pancreas affected by pancreatic fibrosis, VA-lip siRNAgp46 can reduce collagen.

Example 4

Experiment of Regenerative Therapy of Pancreatic Fibrosis Model Rat (1) Preparation of Pancreatic Fibrosis Model Rat Male Lewis rats having a body weight of 150 to 200 g (Charles River) were used. In accordance with a previous report (Inoue et al. Pancreas 2002; 25: e64-70), dibutyltin dichloride (Dibutyltin dichloride, DBTC) was dissolved in 1 part of ethanol and then mixed with 2 parts of glycerol and 2 parts of dimethyl sulfoxide (DMSO) to thus prepare a solution (DBTC solution), and an amount corresponding to 5 mg (DBTC)/kg (body weight) was administered to the rat right carotid artery by means of a syringe.

(2) In Vivo Localization of VA-Lip siRNAgp46-FITC in Rat Pancreas and Other Tissue After 43 days from starting administration of DBTC, at the point when serious pancreatic fibrosis was observed, 1 µL/g body weight of VA-lip siRNAgp46-FITC or Lip siRNAgp46-FITC was administered to the DBTC-treated rat via the tail vein. Administration was carried out under normal pressure three times every other day with 0.75 mg/kg of siRNA each time. 24 hours after the final administration, the rat was sacrificed by perfusion with physiological saline, and the pancreas and other organs (the liver, the lung, the spleen, and the retina) were harvested. The organ samples were fixed with 10% paraformaldehyde, and paraffin-embedded sections were stained using Azan-Mallory stain. Immunohistochemical staining was carried out by the dextran polymer method using each of a monoclonal anti-α-SMA antibody (1:1000, Sigma), an anti-CD68 antibody (1:500, Dako), and an anti-FITC antibody (1:500, Abcam) and by means of an Envision Kit (Dako), and following coloration by means of DAB (Wako Pure Chemical Industries, Ltd., Osaka, Japan) and nuclear staining by means of Gill's hematoxylin solution (Wako Pure Chemical Industries, Ltd.) were carried out.

(3) Western Blotting

In order to evaluate the duration of suppression of expression by means of siRNAgp46 in vivo, protein extracts from the pancreas 0, 1, 2, 3, and 4 days after intravenous administration of VA-lip siRNAgp46 were subjected to Western blotting in the same way as for Example 3. (4).

(4) In Vivo siRNAgp46 Treatment

Three groups of rats (n=6 per group) were used for histological evaluation. 43 days after administration of DBTC, each group was treated with administration of PBS, VA-lip siRNA random, and VA-lip siRNAgp46 10 times respectively (0.75 mg/kg siRNA, administered three times every other day). All administrations were carried out via the tail vein under normal pressure with an amount of 1 µL/g body weight. The pancreas was fixed with 10% paraformaldehyde and embedded in paraffin, and a section was then strained using Azan-Mallory stain and hematoxylin-eosin stain. Immunohistochemical staining was carried out by the dextran polymer method using a monoclonal anti-α-SMA antibody (1:1000, Sigma) and by means of an Envision Kit (Dako), and subsequently coloration by means of DAB (Wako Pure Chemical Industries, Ltd., Osaka, Japan) and nuclear staining by means of Gill's hematoxylin solution (Wako Pure Chemical Industries, Ltd.) were carried out. In order to carry out precise quantitative determination of regions stained by means of Azan-Mallory, hematoxylin-eosin, and α-SMA, six low magnification fields (100×) were randomly selected for each rat pancreatic section and examined using a microscope (Axioplan 2; Carl Zeiss, Inc). A digital image was taken by means of a video recording system using a digital TV camera system (Axiocam High Resolution color, Carl Zeiss, Inc.). The proportion of the region stained by Azan-Mallory and α-SMA in a digital microscope photograph was determined using an automatic software analysis program (KS400, Carl Zeiss, Inc.).

(5) Hydroxyproline Assay

Hydroxyproline content was determined by the Weidenbach method in accordance with a previous report (Weidenbach et al. Digestion 1997; 58: 50-57). In brief, pancreatic cell debris was centrifuged at 3000 rpm for 15 minutes, a pellet was completely hydrolyzed in 6 N HCl at 96° C. for 16 hours, the pH was adjusted to 6.5 to 7.5, and it was subjected again to centrifugation (at 3000 rpm for 15 minutes). 25 µL of an aliquot was dried at 60° C., and the precipitate was dissolved in 1.2 mL of 50% isopropanol and incubated in 200 mL of acetic acid/citric acid buffer (pH 6.0) containing 0.56% chloramine T Solution (Sigma). After incubating at 25° C. for 10 minutes, 1 mL of Ehrlich's reagent was added, and the mixture was incubated at 50° C. for 90 minutes. After cooling, the absorption at a wavelength of 560 nm was measured.

(6) Collagenase Activity of Pancreatic Cell Debris

Measurement of collagenase activity was carried out by a modified method of a previous report (Iredale et al. J. Clin. Invest. 1998; 102: 538-549). In brief, pancreas harvested from a wild-type rat and a pancreatic fibrosis model rat and frozen with liquid nitrogen were crushed on ice in a sample buffer (50 mM Tris, pH 7.6, 0.25% Triton X-100, 0.15 M NaCl, 10 mM $CaCl_2$) containing a serine and thiol protease inhibitor (PMSF 0.1 mM, leupeptin 10 µM, pepstatin A 10 µM, aprotinin 25 µg/mL, iodoacetamide 0.1 mM). The cell debris was centrifuged at 4° C. and 14000 g for 30 minutes, thus removing cell residue and protein aggregate. The collagenase activity in the pancreatic cell debris was determined using an EnzCheck Collagenase Assay Collagen Conjugate kit (Molecular Probes) in accordance with the instruction manual. In parallel thereto, analysis was carried out using an appropriate negative control and positive control (bacterial collagenase), and the results were expressed as fluorescence of degraded collagen per mg of protein (determined by optical density at 280 nm compared with serum albumin standard).

Results

Figure 15:
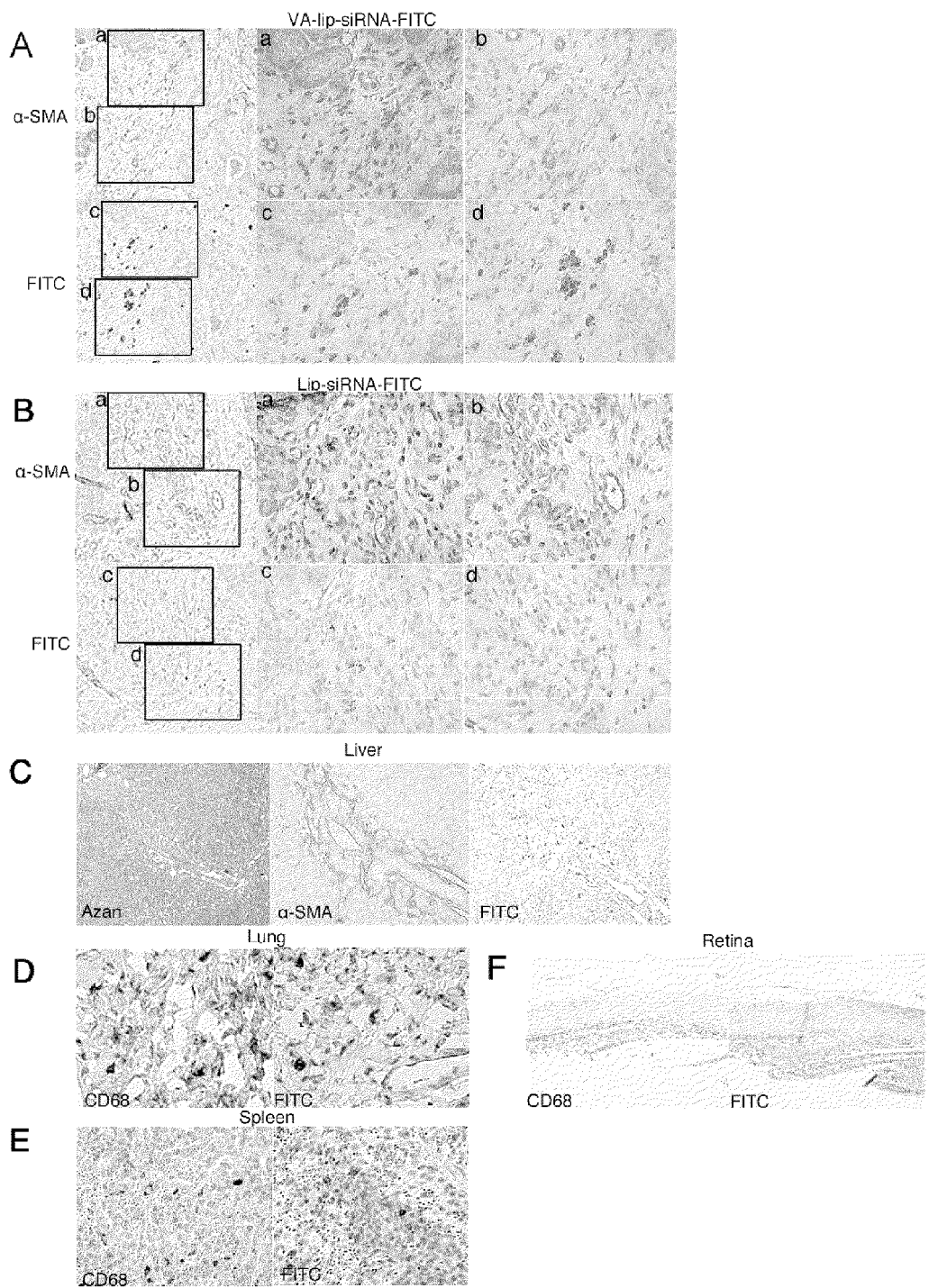
FIG. 15 is a photographic diagram showing the specific delivery of VA-lip siRNAgp46 to pancreatic stellate cells in DBTC-treated rats. A and B are images of immunostaining by an anti-α-SMA antibody and an anti-FITC antibody of rat pancreatic sections that had been treated three times every day with VA-lip siRNAgp46-FITC and Lip siRNAgp46-FITC respectively. Staining images a to d on the right-hand side are enlarged images of regions denoted by the corresponding symbols on the staining image on the left-hand side. C shows images of staining by Azan-Mallory staining, anti-α-SMA antibody staining, and anti-FITC antibody staining of rat liver sections that had been treated three times every day with VA-lip siRNAgp46-FITC. D to F are staining images of staining with an anti-CD68 antibody and an anti-FITC antibody of rat lung, spleen, and retina 24 hours after intravenous administration of VA-lip siRNAgp46-FITC.

In consecutive sections of the pancreas, activated stellate cells and siRNAgp46-FITC were immunostained, and the results were that in the VA-lip siRNAgp46-FITC-treated group, in a region where activated stellate cells (α-SMA-positive cells) aggregated, FITC-positive cells were identified, whereas in the Lip siRNAgp46-FITC-treated group, the number of FITC-positive cells identified in an α-SMA-positive region was very small (FIGS. 15 A and B).

FITC-positive cells in an α-SMA-positive region were also observed in a liver sample (FIG. 15 C). This result coincides with the knowledge that DBTC not only induces pancreatic fibrosis but also hepatic cirrhosis. In other rat organs, including the lung and the spleen, few cells were stained with FITC in a region with macrophage infiltration (CD68-positive cells) (FIGS. 15 D and E), suggesting nonspecific incorporation of siRNAgp46-FITC by macrophages. The retina was negative in FITC staining (FIG. 15 F), and this coincides with the knowledge obtained using VA-lip siRNAgp46-FAM in hepatic cirrhosis. It is thought that the eyeball probably constructs an independent system due to the low permeability of the blood-retina barrier.

It was confirmed from the results of Western blotting that, in vivo also, the effect of siRNAgp46 in suppressing the expression of gp46 continued for at least 3 days (FIGS. 16 A and B).

Figure 17:
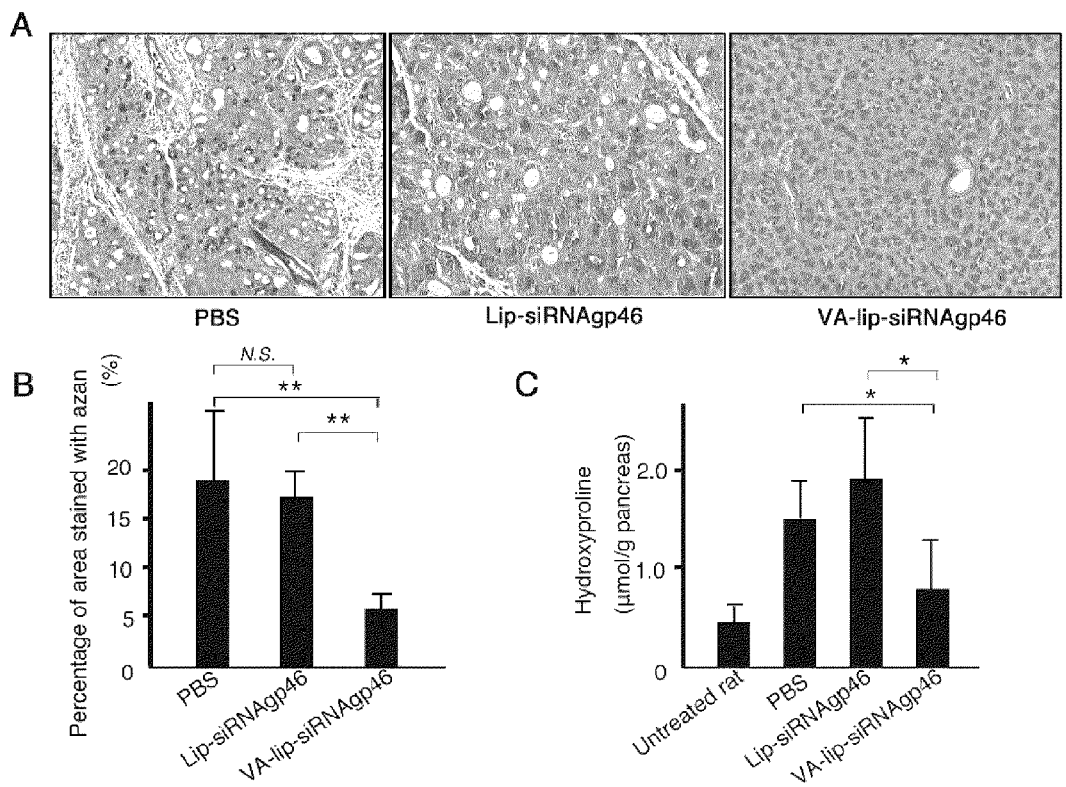
FIG. 17 is a diagram showing the effect of VA-lip siRNAgp46 in DBTC-induced pancreatic fibrosis. A shows Azan-Mallory staining images of pancreatic sections of DBTC-treated rat to which one of VA-lip siRNAgp46, Lip siRNAgp46, and PBS was administered 10 times. B is a graph showing quantification by computer image analysis of regions that showed positive in the Azan-Mallory staining images of A. Data were calculated from 6 fields randomly extracted from six rats of each group and are expressed as average values±standard deviation. C is a graph showing the content of hydroxyproline in the pancreas. Data are expressed as average values±standard deviation.

A DBTC-treated rat to which VA-lip siRNAgp46 had been administered 10 times was evaluated by Azan-Mallory staining (FIG. 17A). The fibrotic region as determined by computer image analysis was markedly reduced in a sample from the VA-lip siRNAgp46-treated group compared with a control sample (P<0.01) (FIG. 17 B). This result coincided with data showing clear suppression of hydroxyproline in the pancreas of the VA-lip siRNAgp46-treated group (FIG. 17 C).

Figure 18:
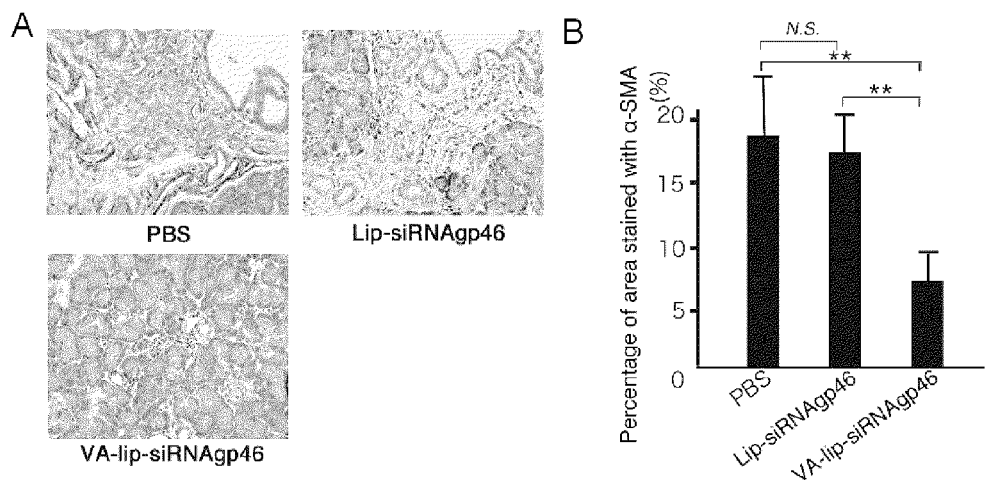
FIG. 18 is a diagram showing the effect of VA-lip siRNAgp46 in DBTC-induced pancreatic fibrosis. A shows α-SMA staining images of the pancreas of DBTC-treated rats after treatment with VA-lip siRNAgp46. B is a graph showing quantification by computer image analysis of α-SMA-positive regions in A. Data were calculated from 6 fields randomly extracted from six rats of each group and are expressed as average values±standard deviation.

In order to evaluate change in stellate cells in the rat pancreas after treatment with VA-lip siRNAgp46, a rat pancreas sample after treatment with VA-lip siRNAgp46 was subjected to α-SMA staining, and the result showed that the number of α-SMA-positive cells markedly decreased compared with that of a rat treated with Lip siRNAgp46 and PBS (FIGS. 18 A and B).

The collagenase activity in pancreatic cell debris of a wild-type rat and a VA-lip siRNAgp46-treated DBTC-treated rat was measured based on the assumption that improvement of fibrosis subsequent to suppression of the secretion of new collagen from PSCs by administration of VA-lip siRNAgp46 involves collagenase derived from inflammatory cells and PSCs themselves, and the results are shown in the table below.

TABLE 1

Collagenase activity in rat pancreatic cell debris

| | Collagenase activity (arbitrary units of fluorescence/mg protein) |
|---|---|
| Normal rat | 20500 ± 300 |
| DBTC rat (29th day) | 26300 ± 700 |
| DBTC rat (57th day) | 25400 ± 1000 |

Numerical values are average values ± standard deviation (n = 5 for each group)

As shown in the table, the collagenase activity in the DBTC-treated rat was almost the same as that of the wild-type rat.

Figure 19:
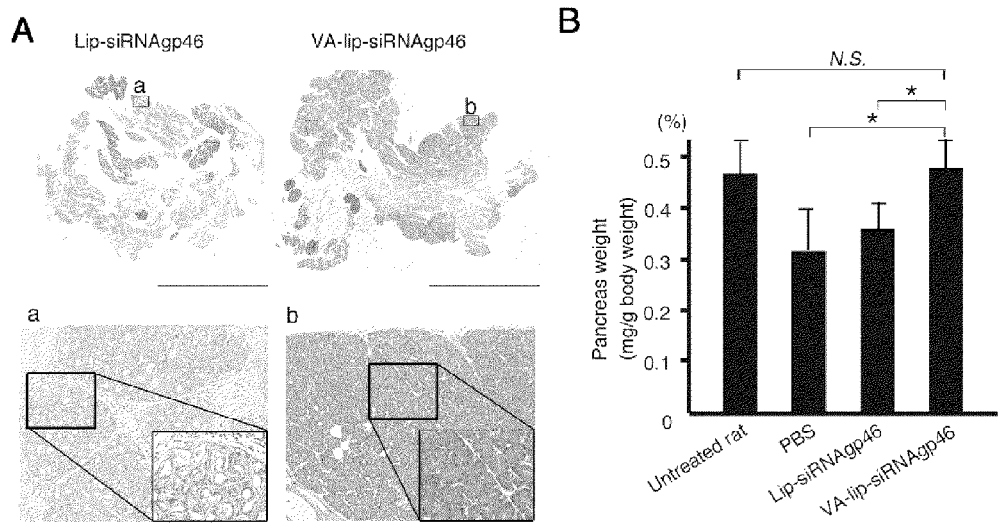
FIG. 19 is a diagram showing the regeneration of normal tissue from fibrotic pancreatic tissue by VA-lip siRNAgp46. A shows hematoxylin-eosin staining images of the pancreas of DBTC-treated rats to which VA-lip siRNAgp46 (right) and Lip siRNAgp46 (left) had been administered 10 times. The bottom diagrams are enlarged diagrams of each region a and b of the top diagrams. B is a graph showing the weight of the pancreas of DBTC-treated rats.

When comparing the hematoxylin-eosin staining images of the pancreatic samples of the VA-lip siRNAgp46-treated and Lip siRNAgp46-treated DBTC-treated rats on the 65th day, in the VA-lip siRNAgp46-treated rat, although not complete, a clear normalization of pancreatic tissue was observed, whereas in the Lip siRNAgp46-treated rat tissue normalization was not observed (FIG. 19 A). This coincided with normalization of the pancreatic weight of the VA-lip siRNAgp46-treated DBTC-treated rat (FIG. 19 B).

Discussion

From the above-mentioned results, it can be seen that due to treatment with VA-lip siRNAgp46, siRNAgp46 is specifically incorporated into activated pancreatic stellate cells (aPSCs) to thus suppress the expression of gp46; as a result, secretion of collagen from aPSCs is suppressed, and a marked effect in the improvement of pancreatic fibrosis is thereby exhibited. Furthermore, a marked decrease in aPSCs was observed, which is probably due to a reduction in the secretion of collagen. It is worthy of special note that treatment with VA-lip siRNAgp46 not only improves pancreatic fibrosis but also induces regeneration of pancreatic tissue. Taking this into consideration together with the results of Example 2 above, these results suggest that reducing collagen accumulated in fibrotic tissue enables normal tissue to be tissue-nonspecifically regenerated from fibrotic tissue.

Example 5

Importance of Space for Growth and Differentiation of Stem Cells

Activated hepatic stellate cells (aHSCs) were cocultured with various densities of hepatic progenitor cells, and the effect of the existence of space around the cells on the differentiation of hepatic progenitor cells was examined. As hepatic progenitor cells, GFP-labeled rat hepatic stem cells obtained in Example 2 (2) above were used, and as the aHSCs, HSCs harvested from an SD rat, cultured, and passaged once were used. The aHSCs were harvested and cultured as follows. First, an SD rat was perfused with EGTA solution and a collagenase solution, the liver was harvested, and the harvested liver was finely cut and filtered using a cell strainer (pore diameter 100 µm). An HBSS+0.25% BSA solution was added to the cell suspension thus obtained, and the mixture was centrifuged at 4° C. and 500 rpm for 2 minutes. The supernatant was harvested and centrifuged at 4° C. and 1300 rpm for 5 minutes. After the supernatant was removed, an HBSS+0.25% BSA solution was added, and a 28.7% Nycodenz solution (Axis Shield, Oslo, Norway) was added so that the concentration of Nycodenz was 13.2%, and mixed. After layering an HBSS+0.25% BSA solution, centrifugation was carried out at 4° C. and 1400×g for 20 minutes. After the centrifugation was complete, an intermediate layer was harvested and cultured using Dulbecco's Modified Eagle's medium (DMEM)+10% fetal bovine serum (FBS) medium for 5 days. Passaging was carried out on the fifth day of culturing, and the cells were used in the present experiment.

aHSCs were sown on cell culture inserts (pore diameter 0.4 μm, BD Falcon, Franklin Lakes, N.J., USA) at a density of $5 \times 10^4$ cells/well and cultured in an incubator at 37° C. and 5% $CO_2$ using DMEM+10% FBS for 48 hours. 2 days after sowing the aHSCs, hepatic progenitor cells were sown on a 24-well plate (BD Falcon) equipped with a type I collagen-coated cover glass (IWAKI, Tokyo, Japan) at a density of $1 \times 10^4$ cells/well (low density) and $5 \times 10^5$ cells/well (confluent). Subsequently, the above-mentioned cell culture inserts containing aHSCs were inserted into the wells of the 24-well plate and cocultured in an incubator at 37° C. and 5% $CO_2$ for 10 days (as medium, DME/F12 (Dulbecco's Modified Eagle's Medium/Nutrient F-12 Ham)+10% FBS+ITS (10 mg/L insulin, 5.5 mg/L transferrin, 0.67 μg/L selenium)+0.1 μM dexamethasone+10 mM nicotinamide+50 μg/mL β-mercaptoethanol+2 mM L-glutamine+5 mM Hepes was used).

On the 10th day of coculturing, immunostaining was carried out using an anti-albumin antibody (rabbit polyclonal, MP Biomedicals), albumin-positive colonies were imaged using an inverted microscope (Nikon) at a magnification of 100×, and based on the image obtained the area of albumin-positive colonies was calculated using NIS-Elements software (Nikon). The results are shown in FIG. 20.

Figure 21:
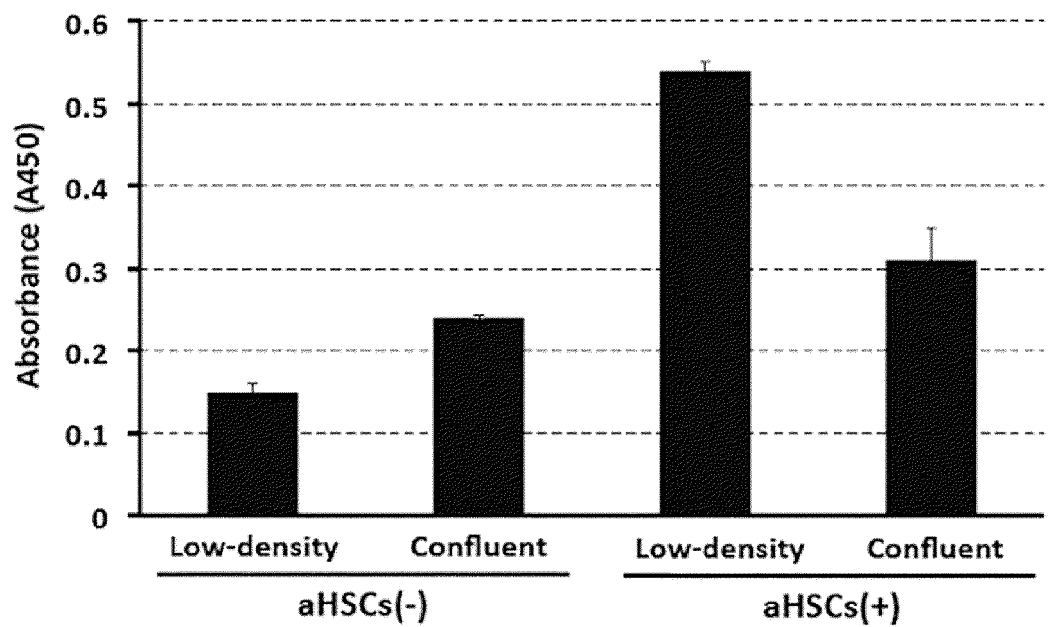
FIG. 21 is a graph showing the effect on the differentiation of stem cells in the presence or absence of space around the stem cells. The ordinate shows an index for the growth rate of stem cells.

In a different experiment, on the 10th day of coculturing, measurement of cell growth was carried out using a Premix WST-1 Cell Proliferation Assay System (Takara, Tokyo, Japan) with a microplate reader (Bio-Rad Laboratories, Hercules, Calif., USA). The results are shown in FIG. 21.

Figure 20:
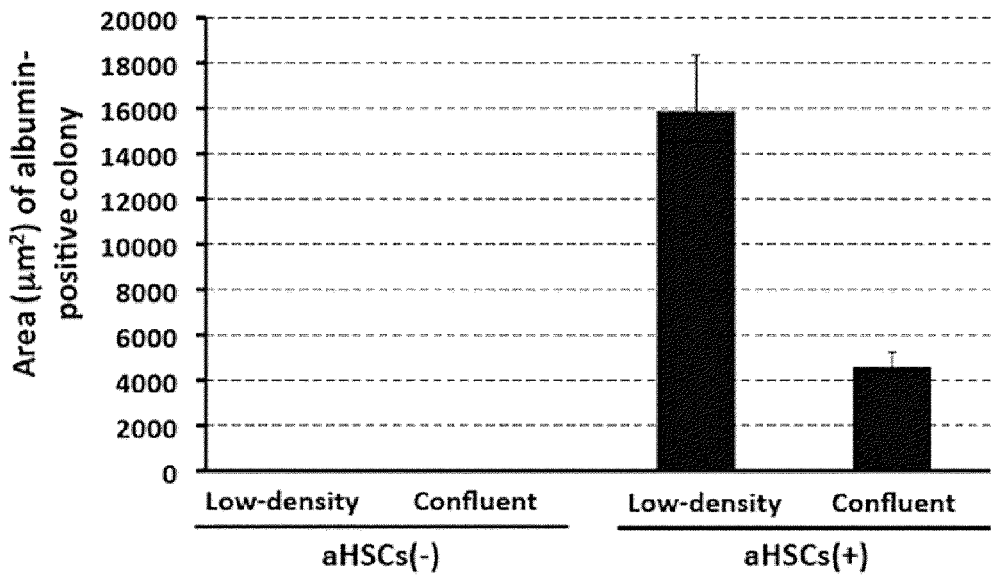
FIG. 20 is a graph showing the effect on the differentiation of stem cells in the presence or absence of space around the stem cells. The ordinate shows albumin-positive colony area.

From the results shown in FIG. 20, it was clear that, when aHSCs were cocultured with hepatic progenitor cells sown at a low density, the hepatic progenitor cells differentiated into a large number of albumin-positive hepatocytes, but when the hepatic progenitor cells were confluent, only a very small number differentiated into hepatocytes. When hepatic progenitor cells were monocultured, they did not differentiate into albumin-positive hepatocytes. Furthermore, as shown in FIG. 21, when the hepatic progenitor cells were sown at the same density as above, the proliferation potency thereof was smaller under confluent conditions than at low density conditions.

From the above results, it has been found that activated stellate cells induce growth and differentiation of stem cells, and the existence of a physical space around stem cells has an important effect on the growth and differentiation of stem cells. When this is taken into consideration together with the results of the Examples above, it shows that a collagen-reducing substance causes a reduction of fibrous tissue in fibrotic tissue, space is formed around stem cells, and as a result the stem cells grow and differentiate, thus regenerating normal tissue.

The invention claimed is:

1. A method comprising identifying a human subject (1) having a fibrotic tissue that continually receives a fibrotic stimulus and (2) for whom regeneration of normal tissue from the fibrotic tissue is needed; and administering an effective amount of a pharmaceutical composition comprising a collagen-reducing substance to the subject, thereby differentiating stem cells into normal tissue cells in the fibrotic tissue and regenerating normal tissue from the fibrotic tissue in the subject while the fibrotic tissue is receiving the fibrotic stimulus.

2. A method comprising identifying a human subject (1) having a fibrotic tissue that continually receives a fibrotic stimulus and (2) for whom regeneration of normal tissue from the fibrotic tissue is needed; reducing collagen in a fibrotic tissue of the subject and/or a step of forming a space for cell growth and differentiation in a fibrotic tissue of the subject; and differentiating stem cells in the fibrotic tissue into normal tissue cells, thereby regenerating normal tissue from the fibrotic tissue while the fibrotic tissue is receiving the fibrotic stimulus.

3. The method according to claim 1, wherein the collagen-reducing substance is selected from the group consisting of a suppressor of collagen production by collagen-producing cells, a promoter of collagen decomposition, and a suppressor of a collagen decomposition inhibitor.

4. The method according to claim 1, wherein the pharmaceutical composition further comprises a targeting agent for collagen-producing cells in fibrotic tissue.

5. The method according to claim 1, wherein the pharmaceutical composition further comprises a retinoid.

6. The method according to claim 3, wherein the suppressor of collagen production by collagen-producing cells is selected from the group consisting of a TGFβ inhibitor, HGF or a substance promoting the production thereof, a PPARγ ligand, an angiotensin inhibitor, a PDGF inhibitor, relaxin or a substance promoting the production thereof, a substance that inhibits the production and secretion of an extracellular matrix component, a cell activity suppressor, a cell growth suppressor, and an apoptosis-inducing substance.

7. The method according to claim 3, wherein the promoter of collagen decomposition is collagenase or a collagenase production promoter.

8. The method according to claim 3, wherein the suppressor of a collagen decomposition inhibitor is a TIMP inhibitor.

* * * * *